US006877530B2

(12) United States Patent
Osborne et al.

(10) Patent No.: US 6,877,530 B2
(45) Date of Patent: Apr. 12, 2005

(54) AUTOMATED MEANS FOR WITHDRAWING A SYRINGE PLUNGER

(75) Inventors: Joel A. Osborne, Oklahoma City, OK (US); William C. Aven, Edmond, OK (US); Dennis Tribble, Oklahoma City, OK (US)

(73) Assignee: ForHealth Technologies, Inc., Daytona, FL (US)

( * ) Notice: Subject to any disclaimer, the term of this patent is extended or adjusted under 35 U.S.C. 154(b) by 0 days.

(21) Appl. No.: 10/457,066

(22) Filed: Jun. 5, 2003

(65) Prior Publication Data
US 2004/0103951 A1 Jun. 3, 2004

Related U.S. Application Data
(60) Provisional application No. 60/470,328, filed on May 13, 2003, and provisional application No. 60/430,481, filed on Dec. 3, 2002.

(51) Int. Cl.[7] .................................................. B65B 1/04
(52) U.S. Cl. ............................ 141/27; 141/25; 141/95; 141/198; 141/330; 604/416
(58) Field of Search ................................ 141/2, 18, 21, 141/25, 27, 94, 95, 192, 198, 391, 330; 604/416

(56) References Cited

U.S. PATENT DOCUMENTS

| 5,805,454 | A | | 9/1998 | Valerino, Sr. et al. |
| 5,900,557 | A | * | 5/1999 | Tanihata et al. ......... 73/863.01 |
| 6,048,086 | A | | 4/2000 | Valerino, Sr. |
| 6,615,881 | B1 | * | 9/2003 | Bartholomew et al. ....... 141/18 |
| 2001/0018937 | A1 | * | 9/2001 | Nemoto ....................... 141/27 |
| 2002/0020459 | A1 | | 2/2002 | Baldwin et al. |

* cited by examiner

Primary Examiner—Timothy L. Maust
(74) Attorney, Agent, or Firm—Darby & Darby

(57) ABSTRACT

In one exemplary embodiment, an automated means for withdrawing a syringe plunger a method for just-in-time extension of the plunger to permit filling the syringe with a prescribed dose of medication are provided. The method includes the steps of: (1) inputting a desired volume of the prescribed dose of medication; (2) inputting syringe identifying information; (3) calculating a distance that the plunger is to be extended based on the inputted desired volume and syringe identifying information; (4) calculating drive parameters for a controllable drive that causes extension of the plunger when actuated and ensures that the plunger is extended the desired distance; and (5) controlling the drive in view of the calculated drive parameters to cause the plunger to be extended the desired distance.

20 Claims, 14 Drawing Sheets

To Air Source

AUTOMATED MEANS FOR WITHDRAWING A SYRINGE PLUNGER

CROSS-REFERENCE TO RELATED APPLICATION

This application claims the benefit of U.S. patent application Ser. No. 60/470,328, filed May 13, 2003, and U.S. patent application Ser. No. 60/430,481, filed Dec. 3, 2002, both of which are hereby incorporated by reference in its entirety.

TECHNICAL FIELD

The present invention relates generally to medical equipment, and more particularly, to an automated apparatus for preparing a syringe including withdrawing a plunger of the syringe to permit the syringe to receive a unit dose of medication.

BACKGROUND

Disposable syringes are in widespread use for a number of different types of applications. For example, syringes are used not only to withdraw a fluid (e.g., blood) from a patient but also to administer a medication to a patient. In the latter, a cap or the like is removed from the syringe and a unit dose of the medication is carefully measured and then injected or otherwise disposed within the syringe.

As technology advances, more and more sophisticated, automated systems are being developed for preparing and delivering medications by integrating a number of different stations, with one or more specific tasks being performed at each station. For example, one type of exemplary automated system operates as a syringe filling apparatus that receives user inputted information, such as the type of medication, the volume of the medication and any mixing instructions, etc. The system then uses this inputted information to disperse the correct medication into the syringe up to the inputted volume.

In some instances, the medication that is to be delivered to the patient includes more than one pharmaceutical substance. For example, the medication can be a mixture of several components, such as several pharmaceutical substances.

By automating the medication preparation process, increased production and efficiency are achieved. This results in reduced production costs and also permits the system to operate over any time period of a given day with only limited operator intervention for manual inspection to ensure proper operation is being achieved. Such a system finds particular utility in settings, such as large hospitals, where a large number of doses of medications have to be prepared daily. Traditionally, these doses have been prepared manually in what is an exacting but tedious responsibility for a highly skilled staff. In order to be valuable, automated systems must maintain the exacting standards set by medical regulatory bodies, while at the same time simplifying the overall process and reducing the time necessary for preparing the medications.

Because syringes are often used as the carrier means for transporting and delivering the medication to the patient, it is advantageous for these automated systems to be tailored to accept syringes. However, the previous methods of dispersing the medication from the vial and into the syringe were very time consuming and labor intensive. More specifically, medications and the like are typically stored in a vial that is sealed with a safety cap or the like. In conventional medication preparation, a trained person retrieves the correct vial from a storage cabinet or the like, confirms the contents and then removes the safety cap manually. This is typically done by simply popping the safety cap off with ones hands. Once the safety cap is removed, the trained person inspects the integrity of the membrane and cleans the membrane. An instrument, e.g., a needle, is then used to pierce the membrane and withdraw the medication contained in the vial. The withdrawn medication is then placed into a syringe to permit subsequent administration of the medication from the syringe. In many cases, the medication in the vial is powdered and must be reconstituted by the addition of a liquid diluent. In this case, the process includes first injecting diluent into the vial, agitating the vial to liquefy its contents, and then removing the liquefied medication from the vial as previously described.

FIG. 1 illustrates an exemplary conventional syringe 10 that includes a barrel 20 having an elongated body 22 that defines a chamber 30 that receives and holds a medication that is disposed at a later time. The barrel 20 has an open proximal end 24 with a flange 25 being formed thereat and it also includes an opposing distal end 26 that has a barrel tip 28 that has a passageway 29 formed therethrough. The passageway 29 is an ANSI standard male luer fitting. One end of the passageway 29 opens into the chamber 30 to provide communication between the barrel tip 28 and the chamber 30 and the opposing end of the passageway 29 is open to permit the medication to be dispensed through a cannula (not shown) or the like that is later coupled to the barrel tip 28.

An outer surface of the barrel tip 28 can include features to permit fastening with a cap or other type of enclosing member. For example, the outer surface can have threads 27 that permit a tip cap 40 to be securely and removably coupled to the barrel tip 28. The tip cap 40 thus has complementary fastening features that permit it to be securely coupled to the barrel tip 28. The tip cap 40 is constructed so that it closes off the passageway 29 to permit the syringe 10 to be stored and/or transported with a predetermined amount of medication disposed within the chamber 30. As previously mentioned, the term "medication" refers to a medicinal preparation for administration to a patient and most often, the medication is contained within the chamber 30 in a liquid state even though the medication initially may have been in a solid state, which was compounded or processed into a liquid state.

The syringe 10 further includes a plunger 50 that is removably and adjustably disposed within the barrel 20. More specifically, the plunger 50 is also an elongated member that has a proximal end 52 that terminates in a flange 54 to permit a user to easily grip and manipulate the plunger 50 within the barrel 20. Preferably, the plunger flange 54 is slightly smaller than the barrel flange 25 so that the user can place several fingers around, against, or near the barrel flange 25 to hold the barrel 20 and then use fingers of the other hand to withdraw or the thumb of the certain hand to push the plunger 50 forward within the barrel 20. An opposite distal end 56 of the plunger 50 terminates in a stopper 59 or the like that seals against the inner surface of the barrel 20 within the chamber 30. The plunger 50 can draw a fluid (e.g., air or a liquid) into the chamber 30 by withdrawing the plunger 50 from an initial position where the stopper 59 is near or at the barrel tip 28 to a position where the stopper 59 is near the proximal end 24 of the barrel 20. Conversely, the plunger 50 can be used to expel or dispense medication by first withdrawing the plunger 50 to a predetermined location, filling the chamber 30 with medication and then applying force against the flange 54 so as to move the plunger 50 forward within the chamber 30, resulting in a decrease in the volume of the chamber 30 and therefore causing the medication to be forced into and out of the barrel tip 28.

As shown in FIG. 2, a conventional vial 60 is formed of a body 62 (i.e., glass) and is sealed with a membrane (septum) 64 across the open end 66 of the body 62. The membrane 64 can be formed of any type of material that is typically used in this setting for sealing a container (e.g., vial 60) yet at the same time permit a user to puncture or pierce the membrane 64 with an instrument to gain access to the inside of the container. In one exemplary embodiment, the membrane 64 is formed of a rubber material that fits across the open end 66 while still providing the necessary seal.

The membrane 64 is securely held in place across the open end 66 by a retainer ring 68 that is itself securely attached to the body 62. The retainer ring 68 circumferentially surrounds a neck formed at the open end 66 and includes an upper section that seats against an upper surface of the membrane 64 and a lower section that engages the body 62 underneath the neck. The retainer ring 68 is open in a middle section thereof such that when the retainer ring 68 is securely attached to the body 62, the retainer ring 68 holds the membrane 64 in place with the membrane 64 being visible in the open middle section of the retainer ring 68. The retainer ring 68 can be attached to the body 62 using any number of conventional techniques, including a crimping process, so long as the retainer ring 68 securely holds the membrane 64 such that a seal results between the open end 66 and the membrane 64.

A safety cap 70 is securely attached to the vial 60 to cover the exposed membrane 64 and further seal the open end 66 of the vial body 62. The safety cap 70 is typically formed of a light, disposable material, such as a plastic, and is attached to retainer ring 68 in a tamper proof manner. For example, the safety cap 70 is attached so that once it is removed, it can not be re-attached to the retainer ring 68. In any event and unless the exact history of the particular vial is know, any vial that is missing a safety cap 70 is ordinarily discarded and not used.

The safety cap 70 is a solid member that extends completely across the exposed portion of the membrane 64 and, preferably, the peripheral edges of the safety cap 70 are downwardly curved so that the peripheral edges overlap the outer peripheral edges of the retainer ring 68. The safety cap 70 contains features that permit it to be attached to the retainer ring 68. One skilled in the art understands the various means of securing the safety cap 70 to the retainer ring 68 and therefore these means are not discussed in any great detail.

Typically, the medication is placed in the syringe when the needle is in place and secured to the barrel tip by drawing the medication through the needle and into the syringe barrel. Such an arrangement makes it very difficult for this type of syringe to be used in an automated system due to the fact that medication is drawn through the small needle into the syringe barrel and therefore this operation is a very time and labor intensive task. What is needed in the art and has heretofore not been available is a system and method for automating the medication preparation process and more specifically, an automated system and method for preparing a syringe including the withdrawal of the syringe plunger.

SUMMARY

The present invention provides an automated system for an automated medication preparation system and includes an automated device for extending a plunger of a syringe a distance determined by the data set specific to the certain syringe being used. The device includes a housing and an adjustable plunger extension mechanism that includes a movable component that intimately engages the plunger so that movement of the component is translated into extension of the plunger. The component also includes a controllable drive that moves the component the defined distance. The automated device further has sensor devices that signal a controller when the component reaches either end of its permitted path of travel. The controller is in communication with the controllable drive to instruct the drive to cease moving the component in the direction of movement when the component reaches the defined distance for the certain syringe.

According to one exemplary embodiment, the controllable drive is a servo motor and a screw drive mechanism that is operatively coupled to the carrier so that actuation of the servo motor is translated into movement of a drive spindle of the screw drive mechanism which in turn causes movement of the component. During operation, the servo motor goes through a series of steps and there is a correlation between the number of steps and the distance that the component is driven which in turn can be equated to the defined distance that the plunger is extended.

Further aspects and features of the exemplary automated safety cap removal mechanism disclosed herein can be appreciated from the appended Figures and accompanying written description.

DETAILED DESCRIPTION OF PREFERRED EMBODIMENTS

Figure 2:
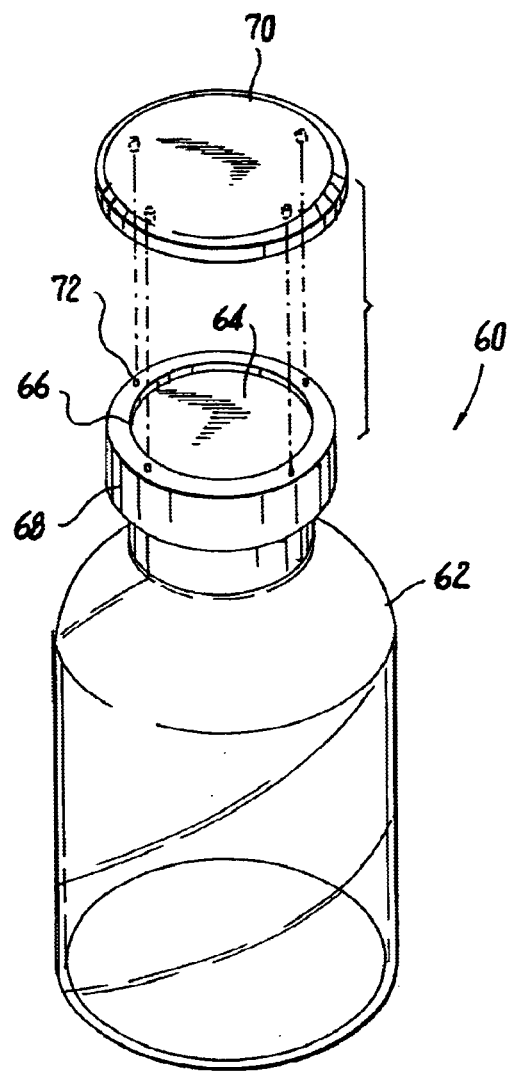
FIG. 2 is a perspective view of a conventional drug vial having a safety cap removed therefrom.
Figure 3:
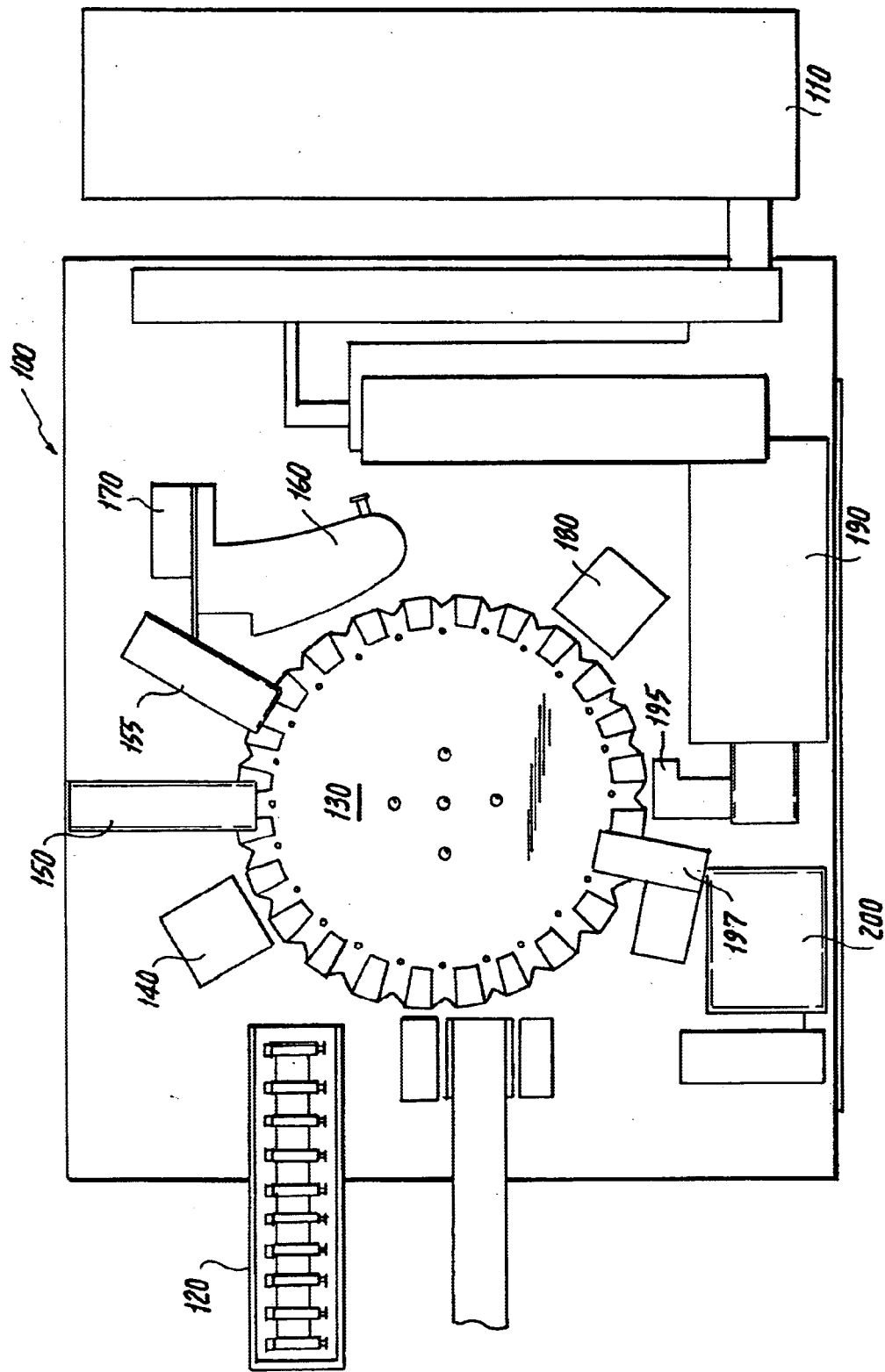
FIG. 3 is a diagrammatic plan view of an automated system for preparing a medication to be administered to a patient.

FIG. 3 is a schematic diagram illustrating one exemplary automated system, generally indicated at 100, for the preparation of a medication. The automated system 100 is divided into a number of stations where a specific task is performed based on the automated system 100 receiving user input instructions, processing these instructions and then preparing unit doses of one or more medications in accordance with the instructions. The automated system 100 includes a station 110 where medications and other substances used in the preparation process are stored. As used herein, the term "medication" refers to a medicinal preparation for administration to a patient. Often, the medication is initially stored as a solid, e.g., a powder, to which a diluent is added to form a medicinal composition. Thus, the station 110 functions as a storage unit for storing one or medications, etc. under proper storage conditions. Typically, medications and the like are stored in sealed containers, such as vials 60 of FIG. 2, that are labeled to clearly indicate the contents of each vial.

A first station 120 is a syringe storage station that houses and stores a number of syringes. For example, up to 500 syringes or more can be disposed in the first station 120 for storage and later use. The first station 120 can be in the form of a bin or the like or any other type of structure than can hold a number of syringes. In one exemplary embodiment, the syringes are provided as a bandolier structure that permits the syringes to be fed into the other components of the system 100 using standard delivery techniques, such as a conveyor belt, etc.

The system 100 also includes a rotary apparatus 130 for advancing the fed syringes from and to various stations of the system 100. A number of the stations are arranged circumferentially around the rotary apparatus 130 so that the syringe is first loaded at a second station 140 and then rotated a predetermined distance to a next station, etc. as the medication preparation process advances. At each station, a different operation is performed with the end result being that a unit dose of medication is disposed within the syringe that is then ready to be administered.

One exemplary type of rotary apparatus 130 is a multiple station cam-indexing dial that is adapted to perform material handling operations. The indexer is configured to have multiple stations positioned thereabout with individual nests for each station position. One syringe is held within one nest using any number of suitable techniques, including opposing spring-loaded fingers that act to clamp the syringe in its respective nest. The indexer permits the rotary apparatus 130 to be advanced at specific intervals.

At the second station 140, the syringes are loaded into one of the nests of the rotary apparatus 130. One syringe is loaded into one nest of the rotary apparatus 130 in which the syringe is securely held in place. The system 100 preferably includes additional mechanisms for preparing the syringe for use, such as removing a tip cap at a third station 150 and extending a plunger of the syringe at a fourth station 155. At this point, the syringe is ready to be filled.

The system 100 also preferably includes a reading device (not shown) that is capable of reading a label disposed on the sealed container containing the medication. The label is read using any number of suitable reader/scanner devices, such as a bar code reader, etc., so as to confirm that the proper medication has been selected from the storage unit of the station 110. Multiple readers can be employed in the system at various locations to confirm the accuracy of the entire process. Once the system 100 confirms that the sealed container that has been selected contains the proper medication, the container is delivered to a fifth station 160 using an automated mechanism, such a robotic gripping device as will be described in greater detail. At the fifth station 160, the vial is prepared by removing the safety cap from the sealed container and then cleaning the exposed end of the vial. Preferably, the safety cap is removed on a deck of the automated system 100 having a controlled environment. In this manner, the safety cap is removed just-in-time for use.

The system 100 also preferably includes a sixth station 170 for injecting a diluent into the medication contained in the sealed container and then subsequently mixing the medication and the diluent to form the medication composition that is to be disposed into the prepared syringe. At a fluid transfer station, the prepared medication composition is withdrawn from the container (i.e., vial) and is then disposed into the syringe. For example, a cannula can be inserted into the sealed vial and the medication composition then aspirated into a cannula set. The cannula is then withdrawn from the vial and positioned using the rotary apparatus 130 in axial alignment with the syringe. The unit dose of the medication composition is then delivered to the syringe, as well as additional diluent if necessary or desired. The tip cap is then placed back on the syringe at a seventh station 180. A seventh station 190 prints and applies a label to the syringe and a device, such as a reader, can be used to verify that this label is placed in a correct location and the printing thereon is readable (station 195). Also, the reader can confirm that the label properly identifies the medication composition that is contained in the syringe. The syringe is then unloaded from the rotary apparatus 130 at an unloading station 200, is weighed to verify fluid transfer, and delivered to a predetermined location, such as a new order bin, a conveyor, a sorting device, or a reject bin. The delivery of the syringe can be accomplished using a standard conveyor or other type of apparatus. If the syringe is provided as a part of the previously-mentioned syringe bandolier, the bandolier is cut prior at a station 197 located prior to the unloading station 200.

Figure 4:
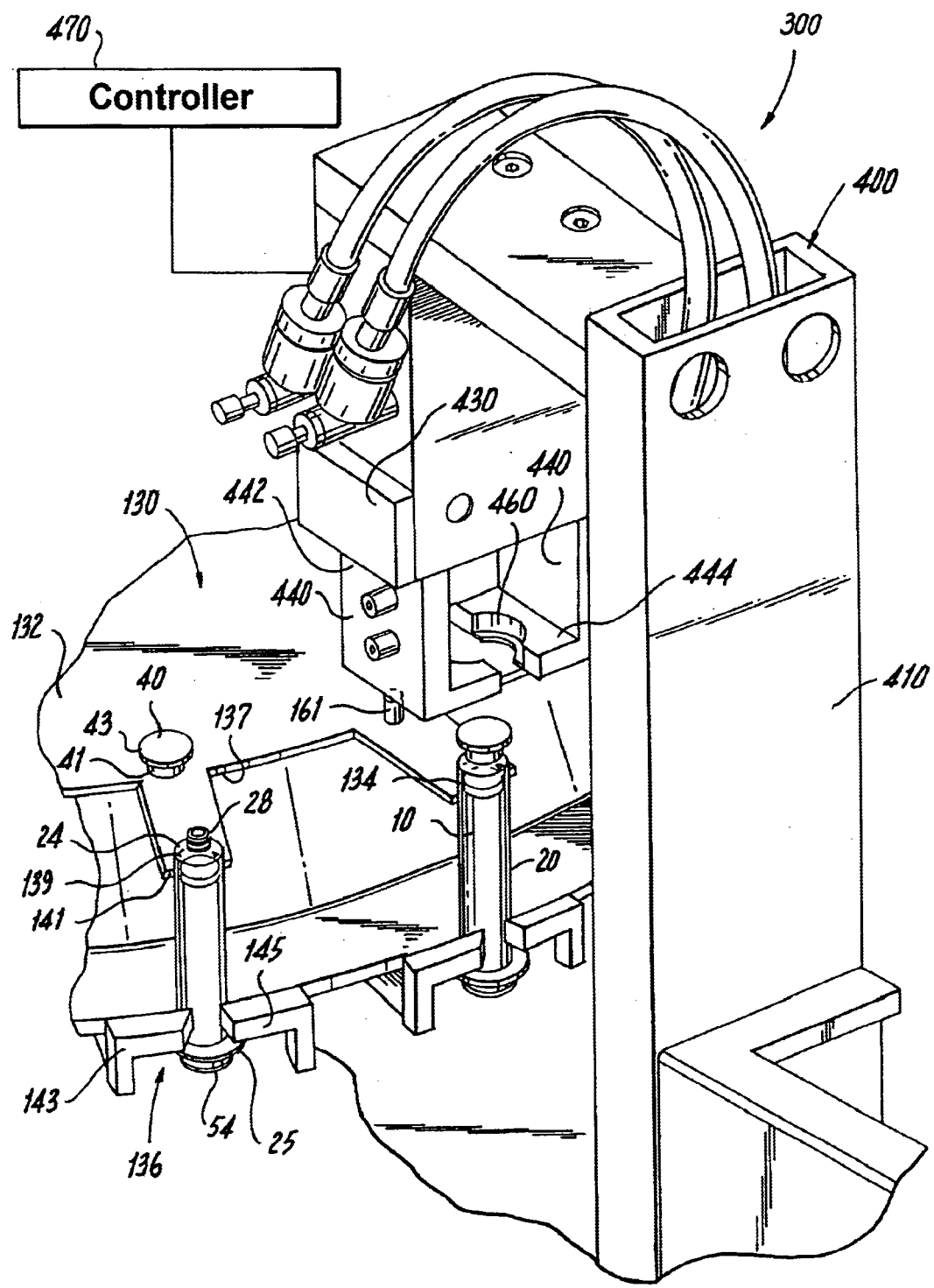
FIG. 4 is a local perspective view of an automated device according to one embodiment for removing the safety tip cap from the syringe.

Referring to FIG. 4, as previously mentioned, one exemplary rotary device 130 is a multiple station cam-indexing dial that is adapted to perform material handling operations. The dial 130 has an upper surface 132 and first and second retaining members 134, 136 for securely holding one syringe 10 in a releasable manner. More specifically, the first retaining member 134 locates the barrel 20 near the distal end 24 thereof and the second retaining member 136 grips and holds the barrel 20 near the proximal end 22 thereof. One exemplary first retaining member 134 includes an arm 135 that is integral to the upper surface 132 of the rotary device 130 and extends outwardly from a main peripheral edge 137 of the dial. The arm 135 has a notch 139 formed at a distal end thereof that is complementary in shape and size to the outer surface of the syringe 10 so that the syringe barrel 20 is received and held within the notch 139. The notch 139 is defined by a pair of opposing fingers 141, with the notch 139 being formed therebetween. One of skill in the art understands that the notch 139 can be formed in a number of different configurations, such as V, U, C, etc. The notch 139 is V-shaped in this exemplary embodiment.

The second retaining member 136 is configured to hold and retain the proximal end 22 of the barrel 20. The second retaining member 136 includes operable pivotable arms 143, 145 that pivot between an open position where the syringe 10 is free to be removed from the dial 130 and a closed position in which the syringe 10 is securely held on the dial 130. A shaped surface 151 also forms a part of the retaining member 136 and is disposed behind the pivotable arms 143, 145. The syringe 10 is disposed between the pivotable arms 143, 145 and the surface 151 and in the retained position, the pivotable arms 143, 145 are in the closed position and the syringe 10 is held securely between the pivotable arms 143, 145 and the surface 151. As will be described in greater detail hereinafter, the controller directs the pivotable arms 143, 145 to either the open or closed positions.

A post 161 is provided for holding the tip cap 40 after its removal to permit the chamber 30 to be filled with medication. One exemplary post 161 has a circular cross-section and is formed near or at the interface between the arm 135 and the dial 130. The post 161 can also be formed on the upper surface 132 of the dial 130. Thus, the precise location of the post 161 can vary so long as the post 161 is located where the tip cap 40 can sit without interfering with the operation of any of the automated devices and also the post 161 should not be unnecessarily too far away from the held syringe 10 since it is desired for the automated devices to travel a minimum distance during their operation to improve the overall efficiency of the system 100. The specific shape of the post 161 can likewise vary so long as the post 161 can hold the tip cap 40 so that it remains on the post 161 during the rotation of the dial 130 as the associated syringe 10 is advanced from one station to another station.

While in one exemplary embodiment, the syringes 10 are fed to the rotary device 130 as part of a syringe bandolier (i.e., multiple syringes 10 are disposed in series and interconnected by a web), it will be appreciated that the syringes 10 can be fed to the rotary device 130 in any number of other ways. For example, the syringes 10 can be fed individually into the rotary device 130 from a loose supply of syringes 10.

Figure 5:
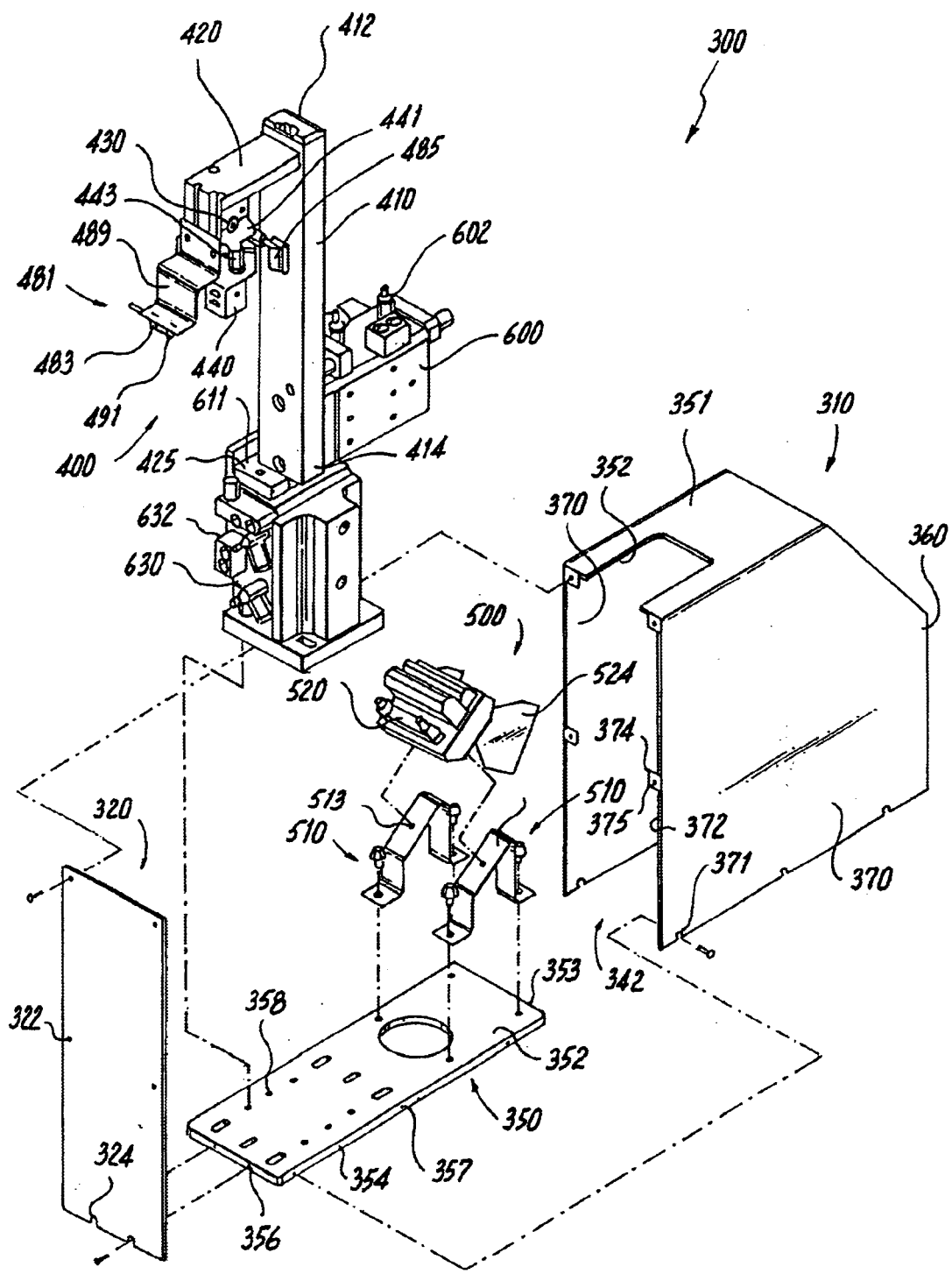
FIG. 5 is an exploded perspective view of an automated device according to another embodiment for removing, parking and replacing the syringe safety tip cap.
Figure 6:
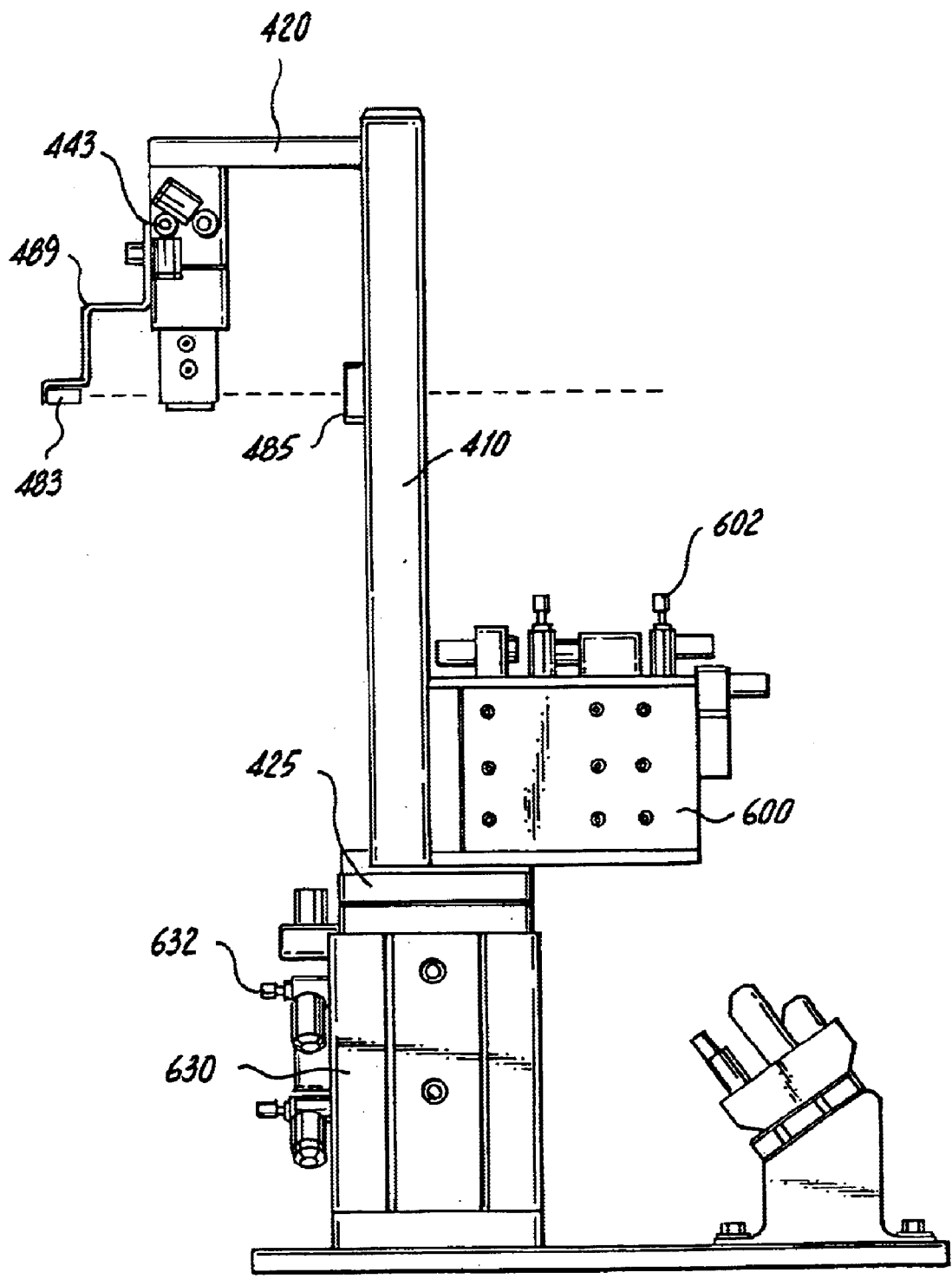
FIG. 6 is a side elevation view of the automated device of FIG. 5.

FIG. 4 is a local perspective view of an automated device 300 according to one embodiment for removing and parking the safety tip cap 40 from the syringe 10. FIG. 4 generally shows some of the major components of the device 300 and its relationship to the rotary device 130 and the syringes 10, while FIGS. 5 and 6 show a detailed construction of device 300 according to one exemplary embodiment.

As will be described in greater detail hereinafter, device 300 is an automated device for the removal, parking and recovery of the tip cap 40. The device 300 includes a pair of operational gripper arms 440 that serve to securely hold the tip cap 40. Each of the gripper arms 440 is a generally F-shaped member that is formed of a vertical section 442 and a horizontal gripping section 444 that extends outwardly from one end of the vertical section 442. The gripping section 444 has a cut-out or notch 460 (FIG. 4) formed therein for receiving and gripping a section of the barrel 20 of the syringe 10. Accordingly, the notch 460 has a complementary shape as the shape of the barrel 20. One exemplary notch 460 has a generally semi-circular shape and it seats against approximately ½ of the outer circumferential surface of the syringe barrel 20. By being movable along at least the y axis, the gripper arms 440 can be positioned either in an open position in which the opposing gripping sections of the arms 440 are spaced apart from one another a sufficient distance to permit the tip cap 40 to be received therebetween or a closed position.

In the closed position, the gripping sections 444 of the arms 440 are brought together so that they either seat against one another or are in very close proximity to one another. When the gripping sections 444 come together in the closed position, the notches 460 define a complete opening that has a diameter about equal to or slightly less than the diameter of the base section 41 of the tip cap 40, thereby permitting the tip cap 40 to nest within the gripping sections 444.

In a first open position of the gripper arms 440, they are spaced sufficiently from one another so as to permit the tip cap 40 to be freely disposed between the gripping sections 444. Using a controller 470 (e.g., a programmable computer, microprocessor, or other unit etc.), the gripper arms 440 are driven to the first position. The controller 470 instructs the gripper unit 400 to perform various operations for removing the tip cap 40 from the barrel tip 28, parking the tip cap 40 on the post 161 and then, at station 180, replacing the tip cap 40 on the filled syringe 10. When such an operation is performed, the vertical base 410 is driven in a number of different direction until proper alignment is realized. In other words, the tip cap 40 is disposed between the gripping sections 444 of the opposing arms 440 and more specifically, the gripping sections 444 are disposed adjacent the base section 41 of the tip cap 40 underneath the flange 43 with the notches being aligned with the outer surface of the base section 41. An actuator or the like (pneumatic) of the device 400 is then activated causing the gripper arms 440 to move inwardly toward one another until the gripping sections 444 seat against the outer surface of the base section 41 of the tip cap 40. In this closed position, the gripper arms 440 apply a force against the base section 41 so that the tip cap 40 is securely held by the gripping sections. When the gripper arms 440 are driven to the closed position, the gripping sections seat against one another and the notches align such that the gripping sections substantially encircle the base section 41.

Figure 1:
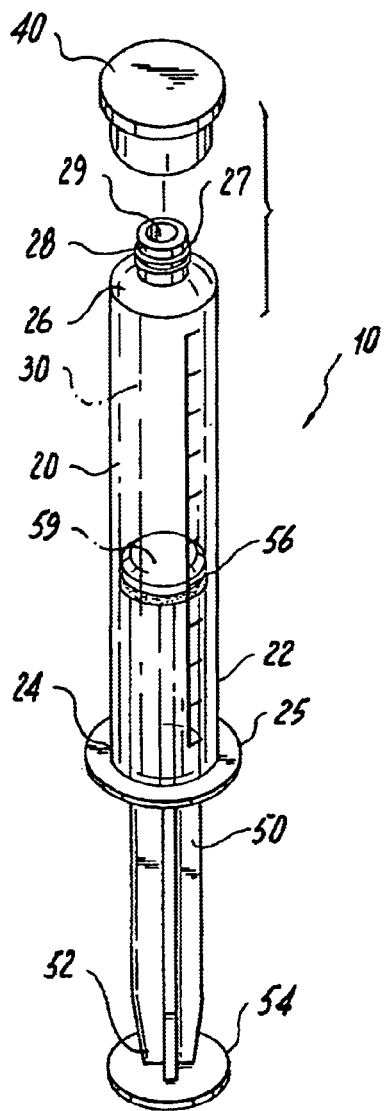
FIG. 1 is a perspective view of a conventional syringe having a safety tip cap removed therefrom.

FIG. 5 is an exploded perspective view of the automated device 300 according to an embodiment that is similar to the general embodiment shown in FIG. 4; however, FIG. 5 illustrates in greater detail the working components for removing, parking and replacing the syringe safety tip cap 40 and FIG. 6 is a side elevation view of the automated device of FIG. 5. The exemplary device 300 is formed of a number of working parts that are operatively connected to one another and are also in communication with the controller 470 that is preferably a programmable unit, such as a personal computer or the like, which controls operation of the device 300 as well as other working components. As best shown in the exploded view of FIG. 4, the device 300 includes a housing 310 and a tip cap gripper unit 400 that engages the tip cap 40 (FIG. 1) and removes it from syringe 10 and then securely places or parks it on the dial 130 before a second device 130 at station 180 retrieves the removed tip cap 40 from the dial 130 and then replacing the tip cap 40 on the syringe 10. The gripper unit 400 is partially contained within the housing 310 except for the adjustable gripper parts that lie outside of the housing 310 so that they can engage and remove the tip cap 40 of one syringe 10 as it is advanced along the dial 130 (FIG. 2).

The exemplary housing 310 includes a front cover plate 320, a back cover 340 and a base plate 350. The front cover plate 320 is a generally rectangular plate that has a number of openings 322 formed therein to receive fasteners (not shown) which securely couple the front cover plate 320 to the back cover 340. The front cover plate 320 can also include one or more slots 324 that also receive fasteners for securely coupling the front cover plate 320 to the base plate 350. For example, the slots 324 can be formed at one edge (e.g., the bottom edge) of the front cover plate 320.

The back cover 340 has a substantially open front face 342 and is formed of a top wall 351, a rear wall 360 and a pair of opposing side walls 370. The top wall 351 has a cut-out 352 formed therein to accommodate movement of the gripper unit 400 within the housing 310. The top wall 351 is generally square or rectangular shaped and extends between the side walls 370 and the rear wall 360. The opposing side walls 370 are mirror images of one another and are disposed parallel to and spaced apart from one another. A front edge 372 of each side wall 370 includes a number of fastening tabs 374 that provide mounting surfaces for securely attaching the front cover plate 320 to the back cover 340. Two of the fastening tabs 374 are located at the intersection between the top wall 351 and the side walls 370 and two additional fastening tabs 374 are located below the two tabs 374 at the top wall 351. The illustrated tabs 374 are generally square shaped and are disposed perpendicular to a plane that contains the respective side wall 370. Openings 375 are formed in the fastening tabs 374 for receiving the fasteners and are axially aligned with openings 322 of the front cover plate 320. The side walls 370 also include fastening slots 371 that receive fasteners for securely attaching the side walls 370 to the base plate 350.

The base plate 350 is securely attached to the side walls 370 and the front cover plate 320. The base plate 350 has a shape and is dimensioned in a complementary manner relative to the other parts of the housing 310. The illustrated base plate 350 is generally rectangular shaped and is formed of a body 352 that includes end edges 353 and side edges 354. The end edges 353 have openings 356 formed therein to receive fasteners for coupling the front cover plate 320 to the base plate 350. Similarly, the side edges 354 have openings 357 that receive fasteners for securely coupling the side walls 370 to the base plate 350. The body 352 also includes openings 358 formed therein for securely mounting various components to the base plate 350. For example, the gripper unit 400 is securely attached to the base plate 350 using fasteners that extend through a number of these openings 358.

Any number of different types of materials can be used for the housing 310 and the shape thereof is also likely influenced by design considerations, such as the amount of available space near the dial 130. Thus, the illustrated housing 310 is merely exemplary in nature and not limiting of the present housing 310. For example, the housing 310 can be formed of sheet metal, etc.

The gripper unit 400 is an assembled unit disposed at the third station 150 that is configured to remove the tip cap 40 from the barrel tip 28 of the syringe 10 and place it or park it on the post 161. The automated gripper unit 400 is a robotic device or an automated mechanical device and preferably, one exemplary automated gripper unit 400 is a pneumatically operated device; however, the gripper unit 400 can be driven by a motor, etc. The automated gripper unit 400 includes a vertical base 410 which is adjustable in at least several directions. For example, the vertical base 410 has an independent reach (y axis) and vertical axis (x axis) which provides part of the flexibility and motion control that is desirable for the unit 400. The vertical base 410 has an upper end 412 and an opposing lower end 414 which is operatively coupled to other movable components, as will be described hereinafter, to permit the vertical base 410 to move in an up/down direction along the x axis and in lateral directions along the y axis. The upper end 412 is connected to a horizontal support member 420 (e.g., a top bracket) that extends outwardly away from the vertical base 410. In one exemplary embodiment, the lower end 414 is securely attached to a support member 425.

A block member 430 is connected to the horizontal support member 420 and more specifically, the block member 430 is disposed on an underside of the horizontal support member 420 so that it is spaced away from the vertical base 410. The exemplary block member 430 has a block-like shape and is connected to the underside of the horizontal support member 420 by one or more connectors, etc.

The gripper unit 400 has first and second positionable gripper arms 440 which are adjustable in at least one direction and which are coupled to and extend downwardly from the block member 430. For example, each of the gripper arms 440 is movable at least in a direction along the y axis to provide the flexibility and motion control that is desirable in the present system 100. The gripper arms 440 are programmed to work together in tandem so that both arms 440 are driven alike (e.g., either toward each other or away from one another) and at the same time.

One knowledgeable in the state of the art will recognize that several motion control devices (i.e., motors, hydraulic drives, pneumatics, etc.) can be used to conduct the linear motion required of the various stations. In the present invention, different motion control devices are used for their defined operations. For stations 150, 180, the motion control devices are powered by pneumatic pressure. Stations 150 and 180 each have three pneumatic motion control devices. For each of these motion control devices, there is a constant pneumatic pressure forcing the certain component to its safe "Home" position and a single state valve that is actuated by input from the system controller 470 that over pressurized, the pneumatic cylinder so that the mechanical component can advance to the endstop opposite to its "Home" position.

The block member 430 can house some of the electronic or pneumatic components and the like that permit the gripper arms 440 to move between the open and closed positions. The coupling between the block member 430 and the gripper arms 440 is such that the gripper arms 440 have the necessary degree of movement to permit the opening and closing thereof.

Since the gripper unit 400 is preferably a pneumatic device, a number of pneumatic controls are disposed near the gripper arms 440. More specifically, the gripper arms 440 are pneumatic devices and therefore, a first pneumatic control 441 is connected to the block member 430. The first pneumatic control 441 is integral to block member 430 and includes first and second flow control valves 443 that are of a point locked type, with the positions set at the time of manufacture. For example, the valves 443 have adjusable knobs that permit a certified field service engineer or technician to adjust the pneumatic pressure that is present at the gripper arms 440 to assist in the opening and closing of the gripper arms 440. As will be appreciated, the unit 400 can be a pneumatically based system since the operation of the vertical base 410 only requires the vertical base 410 to be driven between two fixed positions in one direction of movement.

The gripper unit 400 also preferably includes a sensor assembly, generally indicated at 481, for sensing whether a tip cap 40 is present between the gripper arms 440. One exemplary sensor assembly 481 includes a sensor device 483 and a reflector 485 that is spaced therefrom. The sensor device 483 is formed of one or more sensors that are securely attached to a support bracket 489 that is attached to the block member 430. The support bracket 489 has two sections that each has an L-shape and therefore the bracket 489 resembles a series of steps. A bottommost section 491 of the support bracket 489 is the section that holds the one or more sensors 483. The support bracket 489 is disposed so that the gripper arms 440 lie between the support bracket 489 and the vertical base 410.

According to one exemplary embodiment, the sensors 483 are LED type sensors or the like which emit a light beam in a predetermined direction. There are preferably two LED sensors 483 that emit light beams in a direction toward the gripper arms 440 and more specifically, the light beams are targeted between the gripper arms 440 where the tip cap 40 is to be located when the gripper arms 440 properly grip and retain the tip cap 40.

The reflector 485 is securely attached to the vertical base 410 and is axially aligned with the sensors 483 so that when the sensors 483 are actuated, the light beams are emitted from the sensors 483 and, if no obstruction is present, the light beams pass across the space between the support bracket 489 and the inner face of the rear cover 340. If a tip cap 40 is present between the gripper arms 440, then the light beams of the sensors 483 will be impinged or otherwise broken since the tip cap 40 lies within the path of the light beam when it is securely held between the gripper arms 440. When the tip cap 40 is present, the light beams of the sensors 483 do not make contact with the reflector and therefore, the light beams are not reflected back to the sensors 483. Because the sensors 483 are in communication with the control unit 470, a break in the light beam generates a control signal that is delivered to the control unit 470 to indicate that an object, such as the tip cap 40, is present between the gripper arms 440. Conversely, if the gripper arms 440 are instructed to remove the tip cap 40, they are actuated and moved to a position for gripping and retaining the tip cap 40 and if for some reason, the tip cap 40 is not removed properly, then the sensor's light beam is not impinged by the tip cap 40. The light beam of the sensors 483 pass completely to the reflector 485 since there is no tip cap 40 present between the gripper arms 440. The control unit 470 therefore does not receive the control signal indicating the presence of one tip cap 40 between the gripper arms 440. After a predetermined time period, the control unit 470 will reject the syringe 10 if the presence of the tip cap 40 is not detected. Once the syringe 10 is rejected, the dial 130 is advanced and the tip cap process is started over with the next adjacent syringe 10 on the dial 130 being advanced so that it is in position for the gripper unit 400 to act and remove the tip cap 40. If the sensor device 483 detects the presence of a tip cap 40 at a time when the presence is expected, the control signal from the sensor device 483 is received by the control unit 470 and the gripper unit 400 is instructed to continue its process of removing, parking, or replacing the tip cap 40.

The gripper unit 400 includes a number of pneumatic control devices and more specifically, the gripper unit 400 includes a second pneumatic control device 600 and a third pneumatic control device 630. The second pneumatic control device 600 controls movement of the vertical base 410 in towards and out away from the dial 130. In other words, the second pneumatic control device 600 moves the vertical base 410, as well as the gripper arms 440, in a direction toward the dial 130 and in a direction away from the dial 130. The second pneumatic control device 600 is similar to the previously described motion control device 431 with its "Home" position being out, away from the dial 130.

In the illustrated embodiment, the second pneumatic control device 600 is disposed at a lower end of the vertical base 410 and preferably is operatively coupled thereto so that actuation of the control device 600 causes the selective, controlled movement of the vertical base 410 in and out from the dial 130. As shown in FIG. 6, both the lower end of the vertical base 410 and the second pneumatic control device 600 are disposed on a support surface 611 of the support member 425. More specifically, the support member 425 has one or more guide tracks formed therein to permit the controlled in and out movement of the vertical base 410. As the vertical base 410 moves in the in and out directions, it moves from one end of the support member 425 to the other end of the support member 425 in a controlled manner so that the gripper arms 440 are moved from an out position, where the gripper arms 440 are disposed away from the dial 130 as represented in FIG. 4, to in out position, where the gripper arms 440 are disposed above the dial 130. In this embodiment where pneumatic controls are used, the vertical base 410 travels a fixed distance, namely the distance between the out position and the in position and vice versa.

The second pneumatic control device 600 includes a number of adjustable control features that permit a certified field service engineer or technician to vary the operating parameters of the device 600. For example, the second pneumatic control device 600 can include one or more control valves 602 for controlling and adjusting the pneumatic pressure within the second pneumatic control device 600. In the illustrated embodiment, these control valves 602 are in the form of control knobs that can be easily adjusted by a certified field service engineer or technician.

The third pneumatic control device 630 controls movement of the vertical base 410 in the up-down directions. In other words, the third pneumatic control device 630 moves the vertical base 410, as well as the gripper arms 440, and the second pneumatic control device 600 in a vertical direction. The third pneumatic control device 630 is similar to the previously described motion control device 431 with its "home" position being up, keeping the gripper mechanism 440 away from the dial 130.

In the illustrated embodiment, the third pneumatic control device 630 is disposed below the support member 425 and therefore is generally below the lower end of the vertical base 410. Preferably, the third pneumatic control device 630 is operatively coupled to the support member 425 so that actuation of the third pneumatic control device 630 causes the selective, controlled movement of the vertical base 410 in up-down directions. As previously specified, one knowledgeable in the state of the art recognizes that controlling the vertical motion of certain components connected to the support member 425 can be accomplished by one of a number of motion controllers (i.e., motors, hydraulic lines, pneumatics, etc.). In the present invention, the up-down movement of the vertical base 410 can be caused by a pneumatic cylinder or other moving parts that are pneumatically driven.

As the vertical base 410 moves in the up and down directions, the vertical base 410 is raised and lowered relative to the housing 310 in a controlled manner so that the gripper arms 440 are moved from a raised position, where the gripper arms 440 are disposed a maximum distance away from the upper surface of the dial 130, to a lowered position, where the gripper arms 440 are disposed a minimum distance from the upper surface of the dial 130. This lowered position allows for interaction with the tip cap 40 and either the syringe tip 28 or pin 161. In this embodiment where pneumatic controls are used, the vertical base 410 travels a fixed distance, namely the distance between the raised position and the lowered position and vice versa.

The third pneumatic control device 630 includes a number of adjustable control features that permit a trained and certified field service engineer or technician to vary the operating parameters of the device 630. For example, the third pneumatic control device 630 can include one or more control valves 632 for controlling and adjusting the pneumatic pressure within the third pneumatic control device 630. In the illustrated embodiment, these control valves 632 are in the form of control knobs that can be easily adjusted by a trained and certified field service engineer or technician.

The unit 400 (FIG. 4) also includes a connector module 500 that is disposed within the housing 310 and is securely attached to the base plate 350 using a pair of angled mounting brackets 510. The brackets 510 are spaced apart from one another and are mounted to the base plate 350 using fasteners 352 or the like. Each bracket 510 includes a planar surface 512 that has an opening 513 formed therethrough to receive a fastener for mounting a module 520 to the clamps 510. The module 520 is the input/output connector block for the entire station 150. At each end of the module 520, an end stop 524 is provided for limiting the movement of the module 520. More specifically, the end stops 524 keep the module 520 I/O blocks from sliding off the railed tray to which the module 520 is mounted. The connector module 510 is located adjacent the unit 400 and more specifically, it is located behind the third pneumatic control device 630 (e.g., closer to the rear wall 360). The connector module 510 is thus disposed between the unit 400 and the rear wall 360.

The operation of the gripper unit 400 is now described in detail. To remove a tip cap 40, the third pneumatic control device 630 is deactivated (valve is closed) so that the vertical base 410 and the gripper arms 440 are in the raised position. At the same time, the second pneumatic control device 600 is not actuated (valve closed) and therefore, the vertical base 410 is in the out position. For ease of description, this orientation is referred to as a starting position which permits the dial 130 to be advanced so that one syringe 10 is delivered to a position where the syringe 10 is in axial alignment with the gripper arms 440. The gripper arms 440 are in a closed position in the starting position to permit entry of the tip cap 40 therebetween. In other words, the first pneumatic control 441 is in an deactivated position, thereby causing the two gripper arms 440 to be closed. When the syringe 10 is advanced to a position where the gripper arms 440 are axially aligned with the syringe 10, the syringe 10 likewise is in a start position.

To initiate the tip cap removal cycle, the pneumatic control device 441 is activated so that the gripper arms 440 are opened. The third pneumatic control device 630 is then activated so that the pressure in the valves 632 is released, thereby causing the device 630 to assume the lowered position. In this lowered position, the tip cap 40 of the syringe 10 is disposed between the gripper arms 440 and then the first pneumatic control 441 is deactivated so that the gripper arms 440 are closed and the tip cap 40 is nested within the gripper arms 440. Because of the complementary shape of the gripper arms 440, the tip cap 40 is securely held therebetween and is ready to be removed from the syringe 10.

To remove the tip cap 40 from the syringe 10, the third pneumatic control device 630 is deactivated so that it moves to the raised position. Because the first pneumatic control 441 remains deactivated, the gripper arms 440 remain in engagement with the tip cap 40 as the third pneumatic control device 630 assumes the raised position and this movement in a direction away from the syringe 10 causes the tip cap 40 to be lifted off of the syringe 10 as it is held between the gripper arms 440. It will be appreciated that the sensor device 483 is preferably used to sense whether the tip cap 40 is securely being held by the gripper arms 440. More specifically, the light beam of the sensor 483 is broken when the tip cap 40 comes between the sensor 483 and the reflector 485 and this signals to the controller 470 that an object, e.g., the tip cap 40, is present between the closed gripper arms 440. If the sensor 483 does not detect the presence of a tip cap 40 when the gripper arms 440 are closed in this position, then the controller 470 will cause the vertical base 410 to return to the start position and the removal and parking operations are started again.

For ease of discussion, the controller 470 is discussed as being a master controller that is operatively connected to each of the working components of the present device. This controller is therefore in communication with the working components and receives feedback and signals therefrom as well as sends signals to the various working components to ensure the proper operation thereof. It will be appreciated that there are a number of different ways that the controllers can be arranged. For example, each working component can have its own controller, which in turn is communicatively connected to the other working components through a master controller or the like.

Once the third pneumatic control device 630 reaches the raised position, the second pneumatic control 600 is then actuated and this causes the vertical base 410 to go from the out position to the in position. In the in position, the gripper arms 440 holding the tip cap 40 are disposed immediately above the pin (post) 161 for parking of the tip cap thereon. In other words, movement of the vertical base 410 from the out position to the in position causes the gripper arms 440 to move from a position over the tip cap 40 to a position over the pin 161. The tip cap 40 is now ready for parking on the pin 161.

To park or place the tip cap 40 on the pin 161, the third pneumatic control device 630 is activated (valve is open) so that the third pneumatic control device 630 moves back to the lowered position. In the lowered position, the gripper arms 440 are immediately above the pin 161. The tip cap 40 is also axially aligned on the pin 161 so that release of the tip cap 40 results in the tip cap 40 being held by the pin 161. To release the tip cap 40, the first pneumatic control 441 is activated (valve is opened) so that the gripper arms 440 move from the closed position to the open position. As the gripper arms 440 move apart from one another, the tip cap 40 is released from the grip thereof.

Once the tip cap 40 is securely retained on the pin 161, the third pneumatic control device 630 is deactivated so that the vertical base 410 moves from the lowered position to the raised position where the gripper arms 440 are a significant distance from the dial 130. In addition to the actuation of the third pneumatic control device 630, the second pneumatic control device 600 is deactuated resulting in the vertical base 410 moving from the in position to the out position. This movement facilitates the further advancement of the dial 130 and the syringe 10 since the gripper arms 440 are moved away from the dial 130 so as to not obscure access thereto. It will be appreciated that the vertical base 410 has now reassumed the starting position and the process can be repeated by advancing the dial 130 so that another syringe 10 is brought into place and the various components of the gripper unit 400 are then controlled and moved in the manner just previously described for gripping, removing, and parking the tip cap 40 on the pin 161.

Referring now to FIGS. 7–10 and according to another aspect of the present invention, the system 100 includes an automated device 700 for withdrawing a plunger a predetermined distance to permit the injection of a preselected volume of medication into the barrel 20. In the system configuration of FIG. 3, the device 700 is located at the fourth station 155. More specifically, FIGS. 7 through 10 illustrate a part of the fourth station 155 (FIG. 3) for preparing a syringe for later use and more specifically, an automated device 700 for withdrawing (extending) the plunger 50 of the syringe 10 a prescribed amount after it has had its tip cap 40 removed therefrom.

Figure 7:
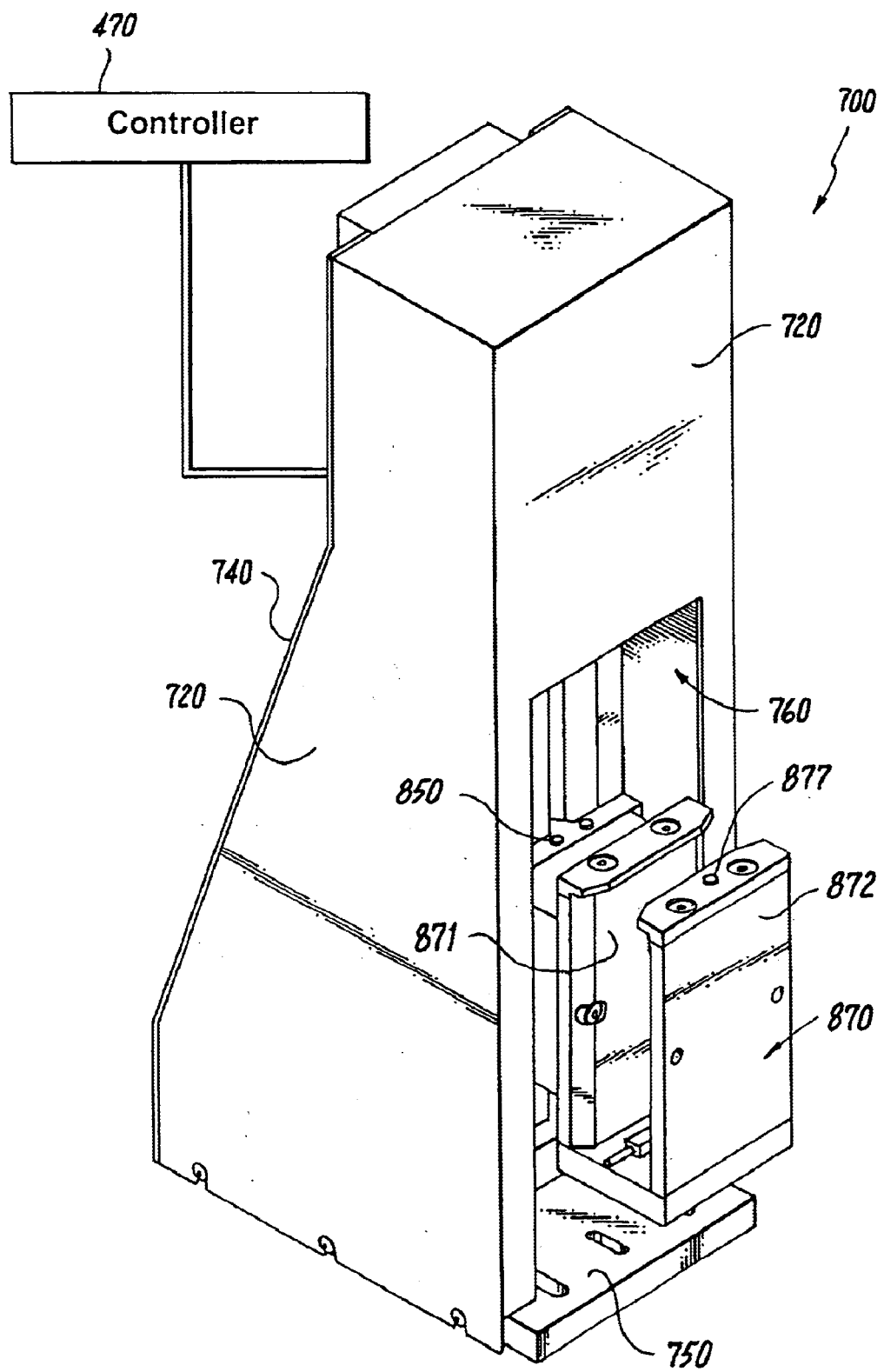
FIG. 7 is a front perspective view of an automated device for withdrawing a plunger of a syringe.
Figure 8:
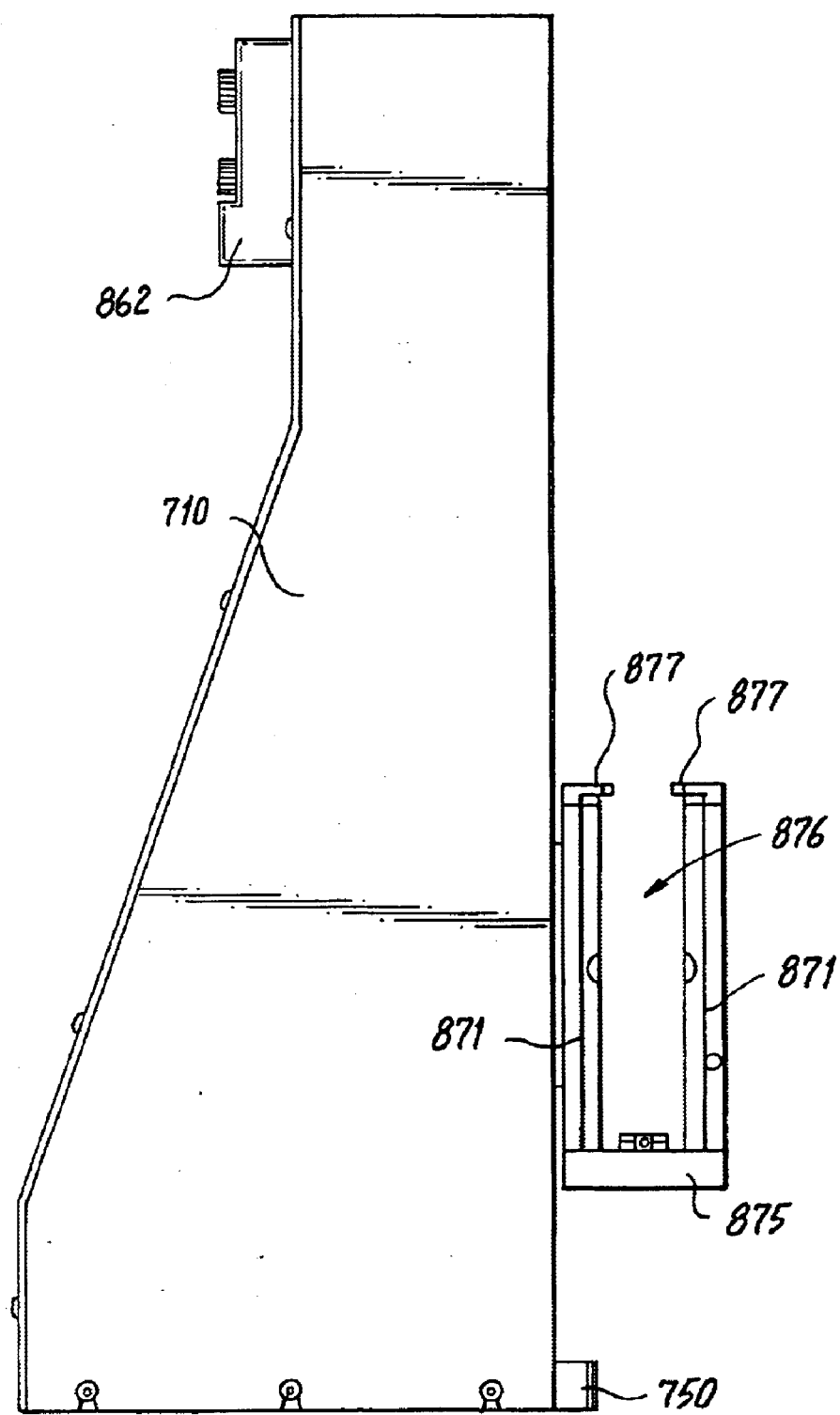
FIG. 8 is a side elevation view of the automated device of FIG. 7.
Figure 9:
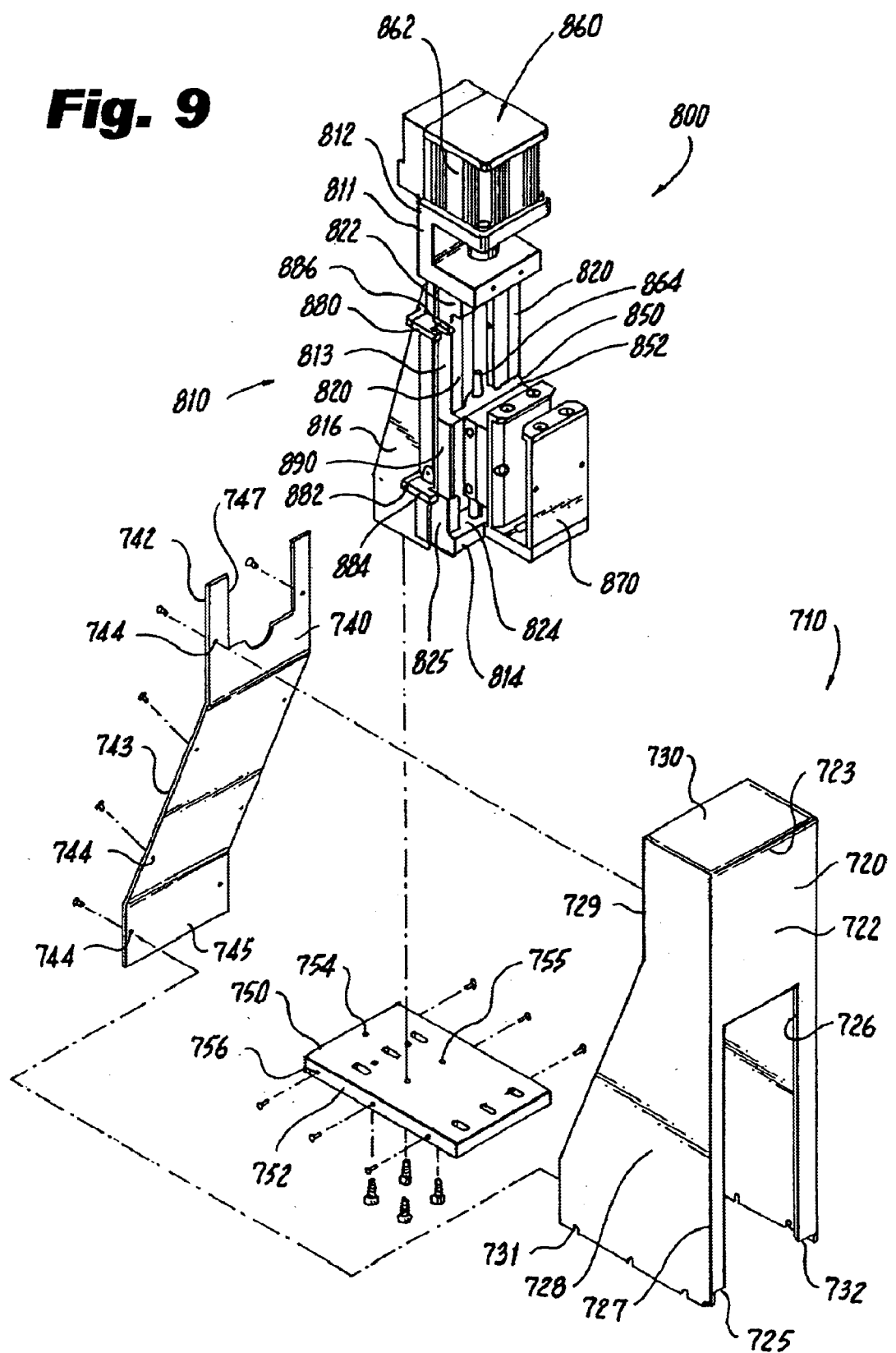
FIG. 9 is an exploded perspective view of the automated device of FIG. 7.

FIG. 7 is a front perspective view of the device 700 and FIG. 9 is an exploded perspective view of the device 700. The exemplary device 700 is formed of a number of working parts that are operatively connected to one another and are also in communication with the controller 470 that is preferably a programmable unit, such as a personal computer or the like, and which controls operation of the device 700. As best shown in the exploded view of FIG. 9, the device 700 includes a housing 710 and a positionable, automated puller 800 that engages the plunger 50 (FIG. 1) and extends it a calculated distance based on a number of parameters that are inputted into the controller 470 as will be described hereinafter in reference to the operation of the device 700. The puller 800 is substantially contained within the housing 710 except for the adjustable puller parts that lie outside of the housing 710 so that they can engage and extend the plunger 50 of one syringe 10 as it is advanced along the dial 130 (FIGS. 2 and 3).

The exemplary housing 710 includes a front cover 720, a back cover 740 and a base plate 750. The front cover 720 has a front face 722 that extends from an upper end 723 to a lower end 725 with a cut out 726 being formed therein and extending from a location proximate the upper end 723 to the lower end 725. In the exemplary embodiment, the front face 722 has a substantially rectangular shape, with the cut out 726 also having a substantially rectangular shape. The front cover 720 also includes two opposing and spaced side faces or walls 728 that are integrally attached to the front face 722 along a front edge 727 (vertical edge) thereof. The side walls 728 also include a rear edge 729 that is integrally attached to the back cover 730. Unlike the front edge 727, which is linear in nature, the rear edge 729 is not linear in nature but rather has an irregular shape (e.g., non-linear). The front cover 720 also includes an upper face or wall 730 that is integrally attached to the upper edges of the front face 722 and the side walls 728. The front cover 720 is constructed preferably as a single integral unit and a slight gap 732 is formed between the lower end 725 of the front face 722 and a ground contacting surface for receiving and permitting the base plate 750 to be securely attached to both the front cover 720 and the back cover 740. The gap 732 is formed because the height of the front face 722 is less than the height of the side walls 728; however, they are each integrally connected to the upper wall 730 and therefore, the gap 732 is formed at the bottom of the housing 710.

The front cover 720 has a number of features formed therein for coupling the front cover 720 to other parts. For example, the side walls 728 can include openings or slots 731 for receiving fasteners to securely attach the side walls 728 to the base plate 750.

The back cover 740 has a shape complementary to the rear edge 729 to permit the back cover 740 to seat against and be securely attached to the side walls 728 at the rear edges 729 thereof. The exemplary back cover 740 has an angled or beveled construction and is generally formed of a first section 742 that is securely attached to the rear edges 729 of the side walls 728. The back cover 740 also includes second and third sections 743, 745, respectively. The second section 743 is an intermediate section that lies between the first and third sections 742, 745. The first section 742 is disposed at the upper end of the housing 710 where the upper wall 730 is located. In the assembled state, the first section 742 is substantially perpendicular to the ground contacting surface, as well as the base plate 750. The first section 742 has a cut out 747 formed therein to permit access to the interior of the housing 710. The first section 742 also includes openings 744 for receiving fasteners to securely attach the first section 742 to the side walls 728.

The second section 743 does not lie within the same plane as the first and third sections 742, 745. The second section 743 is generally rectangular in shape and is a beveled surface with respect to the first and third sections 742, 745. When the back cover 740 is attached to the side walls 728, the second section 743 seats against a complementary shaped beveled surface that forms a part of the rear edges 729 of the side walls 728. The second section 743 also includes openings 744 for receiving fasteners to securely attach the second section 743 to the rear edges 729 of the side walls 728.

Similar to the first section 742, the third section 745 is substantially perpendicular to the ground contacting surface, as well as the base plate 750. The first and third sections 742, 745 thus lie in planes that are substantially parallel to one another; however, the planes are off set or spaced apart from one another. The third section 745 also includes openings 744 for receiving fasteners to securely attach the third section 745 to the rear edges 729 of the side walls 728. When the back cover 740 is securely attached to the front cover 720, an interior compartment 760 is formed and is configured to receive the puller 800.

The base plate 750 serves as the bottom of the housing 710 and is sized and configured to be received between the side walls 728 and within the gap 732. In one exemplary embodiment, the base plate 750 is generally square or rectangular shaped. The base plate 750 has a number of features formed therein to facilitate attachment of the base plate 750 to the side walls 728 (as well as the attachment of the puller 800 to the base plate 750). The base plate 750 has two opposing side edges 752 and a body 754 with the opposing side edges 752 having openings 756 formed therein to receive fasteners. The fasteners extend through the openings or slots 731 formed in the side walls 728 and then through the openings 756 to provide a secure attachment between the side walls 728 and the base plate 750. The body 754 has a number of openings, channels and/or slots 755 formed therethrough. For example, there are a number of thru openings 755 that receive fasteners that threadlingly mate with complementary features formed in the puller 800, to thereby securely attach the puller 800 to the base plate 750.

To assemble the housing 710, the base plate 750 is disposed between the side walls 728 so that one end region of the base plate 750 is disposed underneath the lower edge of the front face 722. The openings 731, 752 are aligned to permit connection between the base plate 750 and the side walls 728. Since the base plate 750 is perpendicular to the other housing components which are vertical in nature, the base plate 750 provides a support platform for the device 700. The back cover 740 can then be attached to the side walls 728 of the front cover 720 in the manner described hereinbefore after the puller 800 has been securely mounted to the base plate 750 as will be described hereinafter.

Any number of different types of materials can be used for the housing 710 and the shape thereof is also likely influenced by design considerations, such as the amount of available space near the dial 130. Thus, the illustrated housing 710 is merely exemplary in nature and not limiting of the present housing 710. For example, the housing 710 can be formed of sheet metal, etc.

The puller 800 is an assembled unit that serves to engage the plunger 50 (FIG. 1) and extend it a calculated distance. The puller 800 has a support frame 810 that has a first end 812 and an opposing second end 814 and a carrier 850 that is controllably movable along a length of the support frame 810 by way of a drive means, generally indicated at 860. The carrier 850 supports a plunger gripper 870 which serves to engage and extend the plunger 50 (FIG. 1) as will be described in greater detail hereinafter.

The support frame 810 has a first section 811 at or near the first end 812 for supporting the drive means 860 and a second section 813 that is disposed underneath the first section 811 and extends to the second end 814. A mounting base 816 is also provided as part of the support frame 810 and is integrally connected to the second section 813. A bottom face of the mounting base 816 receives the fasteners resulting in the unit 800 being securely attached to the base plate 750. Thus, the support frame of the unit 800 is fixed stationary within the interior compartment of the housing 810 and the principle moving parts are the carrier 850 and the plunger gripper 870 that is mounted thereto, as well as parts of the drive means 860.

The second section 813 acts as a support section as well as a guide section since it restricts the movement of the carrier 850 to an up and down (vertical) movement along the length of the vertical second section 813. The second section 813 includes two opposing end posts 820 that are preferably in the form of elongated posts or rails that are arranged in a vertical orientation. In the illustrated embodiment, the rails 820 have a substantially rectangular cross-sectional shape. The rails 820 extend between a first horizontal member 822 and a second horizontal member 824 at the second end 814 of the housing 810. The rails 820 are spaced apart from one another so that a space is formed therebetween and an outermost edge 825 of each rail 820 is a smooth surface to permit the rear face of the carrier 850 to move therealong.

The drive means 860 is a device which, when actuated, drives the carrier 850 in one of two directions vertically along the second section 813. More specifically, actuation of the drive means 860 in a first mode causes the carrier 850 to move in a first direction (up or down direction) and actuation of the drive means 860 in a second mode causes the carrier 850 to move in an opposing second direction (the opposite up or down direction) along the second section 813. One exemplary drive means 860 is a screw drive mechanism that includes a motor 862 that is operatively connected to a screw drive type mechanism. More specifically and according to one exemplary embodiment, the motor 862 is a servo (stepper) motor and the screw drive mechanism includes a drive spindle or drive cable that includes screw coils. The use of a screw drive mechanism is conventional and therefore, the present screw drive mechanism is not described in great detail.

As the drive spindle or drive cable is turned around (rotated) its lengthwise direction, the screw coil "migrates" in the lengthwise direction for displacing the carrier 850 vertically (either up or down) along a length of the second section 813. When the drive spindle is turned around (rotated) in an opposite direction, the carrier 850 moves in the opposite vertical direction. One part 864 of the screw drive means 860 is disposed between the two spaced rails 820. The part 864 is also an elongated member that is disposed between the two rails 822 in a parallel manner.

The first section 811 is generally in the form of a U-shaped member defined by two legs 815 and a wall 817 extending between and connecting the two legs 815 to one another. The first section 811 has a through bore or opening formed therethrough with the drive means 860 disposed adjacent one leg 815 of the first section 811. The first section 811 is also attached securely to the second section 813. The opening thus extends through both legs 815.

The carrier 850 is formed of a body that has a first end and an opposing second end with the first end facing the motor 862 and the second end facing the second horizontal member 824. The carrier 850 has a front face that is securely attached to the plunger gripper 870 using fasteners or other means. The elongated part 864 is operatively coupled to the first end of the carrier 850 so that actuation of the motor 862 and rotation of the drive spindle is translated into up or down movement of the carrier 850 as is the case in a screw drive mechanism where the screw drive spindle drives a carrier or the like. The carrier 850 also includes two side edges 852 that preferably do not extend beyond the two rails 822.

The puller 800 also has an indicator feature for notifying the controller 470 that the carrier 850 has reached one end of its permitted length of travel. For example, the puller 800 can have a first sensor 880 at one end of the permitted length of travel and a second sensor 882 at an opposite end of the permitted length of travel. More specifically, the first sensor 880 and the second sensor 882 are of the types that have a beam that extends across a gap from one section of the sensor to another section of the sensor and the sensor is triggered when an object breaks the beam by passing through this gap. In one exemplary embodiment, each of the first and second sensors 880, 882 is a U-shaped bracket sensor having spaced apart arms 884 that define a gap or space 886 therebetween. The beam extends across the gap 886 from one arm 884 to the opposing arm 884 and the sensors 880, 882 are in communication with the controller 470 so that once an object impinges the beam, a signal is sent to the controller 470 to indicate the occurrence of such event.

The indicator feature also includes a flag or marker 890 that is part of the carrier 850 for tripping one of the sensors 880, 882 when the carrier 850 is in either a maximum up position or a maximum down position. For example, the flag 890 can be a member that is secured to the carrier 850 at one side edge 852. Because the side edges 855 preferably do not extend beyond the two rails 822, the flag 890 is L-shaped with one section being secured to the front face 854 of the carrier 850 and another section that is perpendicular to the one section being disposed parallel to and spaced from the respective side edge 852. The flag 890 is configured and mounted to the carrier 850 so that it is axially aligned with the respective gaps 886 of the two sensors 880, 882 and therefore, as the carrier 850 travels either in an up or down direction, the flag 890 will at some point enter one of the gaps 886 and break the beam that passes across the respective sensor 880, 882. As soon as the flag 890 breaks the beam, a signal is sent from the respective sensor 880, 882 to the controller to indicate that such an event has occurred and the controller 470 will then take the necessary steps to stop further movement of the carrier. In other words, the tripping of the sensors 880, 882 is an event that only occurs when the carrier 850 and surrounding components have been driven to its maximum up or down positions and in order to protect the integrity of the carrier 850, the drive mechanism and the other operative and non-operative parts of the puller 800, the controller 470 will instruct the motor 864 to stop its drive action, thereby preventing the carrier 850 from continued movement in the same direction. Because the portion of the flag 890 that breaks the beam is a vertical wall, an upper edge of this vertical wall is the section that breaks the beam in the sensor 880 and a lower edge of this vertical wall is the section that breaks the beam in the sensor 882. The height of the vertical wall of the flag 890 is approximately equal to the height of the carrier 850 so that the flag 890 trips the sensors 880, 882 before any section of the carrier before or below the flag 890 can strike another object due to excessive travel. The distance between the sensors 880, 882 is predetermined so that it correlates to the maximum up position and maximum down position of the carrier 850 and the normal operation positions of the carrier 850 lie linearly along the second section 813 between the two sensors 880, 882. The sensor 880, 882 are thus mounted to the puller 800 in locations that are laterally beyond the rails 822 so that the sensors 880, 882 do not interfere with the up and down traveling of the carrier 850.

The puller 800 includes the plunger gripper 870 that is securely mounted to the carrier 850 such that movement of the carrier 850 is directly translated into the same directional movement of the gripper 870. The exemplary gripper 870 is a generally U-shaped member having first and second vertical walls 871, 872 that have first ends 873 and opposing second ends 874. At the second ends 874 thereof, the vertical walls 871, 872 are attached to a horizontal wall 875 that extends between the vertical walls 871, 872 and serves to space the walls 871, 872 from one another. A space 876 is thus formed between the vertical walls 871, 872 and this space 876 is open at the ends of the vertical walls 871, 872 so that an object can be received at one end and pass into the space before exiting the space 876 at the other end.

Figure 10:
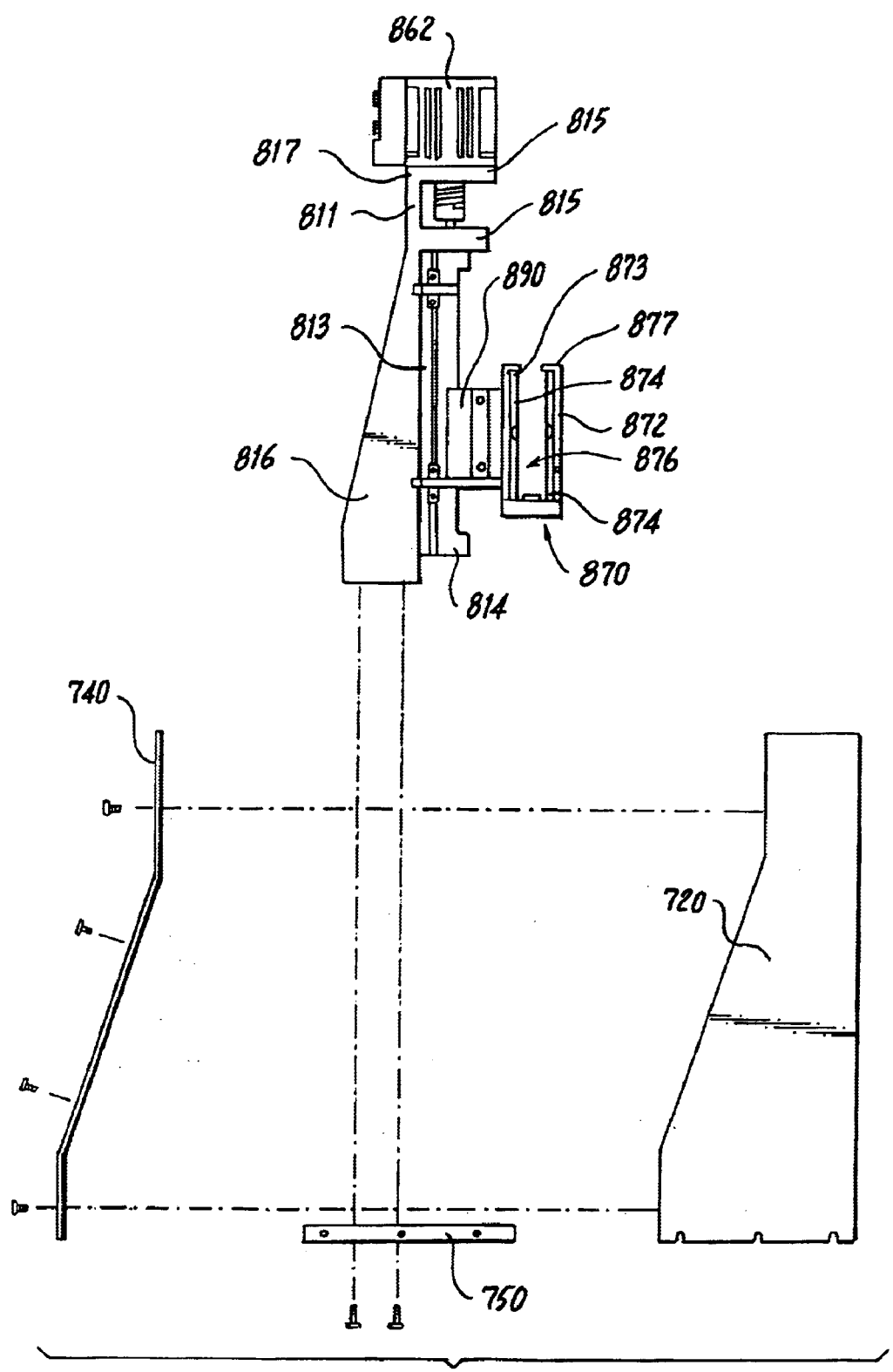
FIG. 10 is an exploded side elevation view of the automated device of FIG. 7.

At the first ends 874, the vertical walls 871, 872 are attached to flange members 877. Each flange member 877 is configured and mounted to one of the vertical walls 871, 872 so that a portion (edge) of the flange member 877 extends beyond the periphery of the vertical wall 871, 872 and into the space 876. In other words, the flange members 877 overhang respective vertical walls 871, 872 as best shown in FIG. 10. The distance between the flange members 877 is thus less than a distance between the vertical walls 871, 872. This distance between the flange members 877 is selected in view of the diameter of the plunger 50 such that the diameter of the plunger 50 is greater than the distance between the flange members 877 and therefore when the plunger 50 is disposed on the underside of the flange members 877 it is unable to travel between the flange members 877 even if a force is applied thereto. The distance between the vertical walls 871, 872 is great enough to receive the plunger 50 and therefore, the syringe 10 can be introduced into the space 876 at one end with the plunger 50 lying within the space 876 before the flange members 877 engage the plunger 50 and cause the extension thereof as will be described hereinafter.

The actuation of the drive motor 862 causes the drive mechanism to be driven and this is translated into controlled movement of the carrier 850 and the plunger gripper 870. The carrier 850 is driven a predetermined distance and to a predetermined location by utilizing the precise controllability of the drive motor 862. More specifically, the drive motor 862 is preferably a conventional servo motor and therefore the actuation of the drive motor 862 causes the drive motor 862 to undertake an operating movement which is represented by a number of steps of the drive motor 862. In other words, the number of steps that the drive motor 862 goes through is continuously determined, monitored and controllable. The drive motor 862 is preferably in communication with the main controller 470 and control signals can be sent from the controller 470 to the drive motor 862 to control the operation thereof.

According to the present invention, the degree of movement of the carrier 850 and the number of steps of the drive motor 862 is calibrated so that the number of steps of the drive motor 862 is equated to the carrier 850 moving a predetermined distance. For example and for a specific syringe type, the drive motor 862 being driven through 20,000 steps causes the carrier 450 to move 5 cm. These measurements are specific to a given type of syringe 10.

The operation of the puller 800 will now be described in greater detail. At the beginning of each operation, the carrier 850 is in the up (top) position. Because the master controller 470 is preferably a programmable unit, the user can input information about a number of different types of syringes that can be used in the present system or filling instructions. For example, there is a useful feature of the present device that involves the ability to set an overdraw on the syringe. The device installation includes an adjustment that "teaches" it where the fully extended (10 ml) position is on the syringe. The controller software determines all other volumetric positions from that position. As a result, teaching the device that the 10 ml position is actually at 10.4 ml, for example, the controlling software in the OCX can cause all positioning to be overdrawn by 0.4 ml. This is useful in adding a slight air gap at the top of the syringe to prevent overfilling and splashing as the syringe is filled.

Further, the amount or distance that the carrier 850 is driven depends upon the desired volume of fluid that is to be injected into the syringe 10, any additional filling specifications, and also depends upon the precise characteristics of the syringe 10. For example, the user may program the controller 470 to fill the syringe 10 with 10 ml of medication and upon receipt of this request, the controller 470 (e.g., the CPU thereof) calculates the distance that the plunger 50 needs to be extended in order for 10 ml to be received within the barrel 20 based on specific syringe product information inputted by the user as described above. Because there is a correlation between the number of steps that the drive motor 862 is driven through and the distance that the carrier 850 is driven, the master controller 470 instructs the drive motor 862 to be driven through a predetermined, specific number of steps that corresponds to the carrier 850 being driven precisely the distance that is equated with the syringe 10 receiving 10 ml of medication. For example, the predetermined distance that the carrier 850 is to be driven to receive the 10 ml medication can be 5 cm and therefore, the drive motor 862 is driven 20,000 steps, which correlates with the carrier 850 moving precisely 5 cm. If the user instructs only 5 ml of medication to be injected into the syringe 10, the master controller 470 will recalculate the necessary distance for the plunger 50 to be extended and the number of steps through which the drive motor 862 is driven which will result in the carrier 850 being moved the necessary distance to ensure that the plunger 50 travels the desired distance.

Unlike many of the conventional automated systems, the present system provides many more options for the user and also permits the distance that the plunger is extended to be readily changed. More specifically, the user only has to input the necessary information, such as the syringe type, and because the controller is a programmable unit, it includes databases of information. The controller accesses these databases and is able to retrieve the syringe characteristics based on the limited information that the user provided. For example, the barrel diameter and the volume specifics about the barrel are determined and then based on the inputted desired (target) volume of the prescribed dose, the controller computes the distance that the plunger needs to be extended in order to form a dosage receiving space of sufficient and optimal dimension. The distance that the plunger is extended can thus be readily changed since it is not restricted to any type of mechanical adjustment but rather it is only determined by the information inputted by the user and therefore it can be readily changed. For example, the user can input a sequence of commands to cause the same type of syringe to be prepared differently in two different batches, namely, a first batch in which the plunger is extended a first distance (to receive first dose volume) and a second batch in which the plunger is extended a second distance (to receive a second dose volume). Conventional devices do not offer such versatility since they are typically arranged or mechanically set to perform a given task, i.e., extend the plunger only one distance.

The software of the programmable controller is written so that it contains calibration tables for various syringe types. In other words, for any given syringe, a predetermined distance that the plunger 50 is moved is equated to a predetermined volume of medication that is received within the plunger 50. For example, extending the plunger 50 of a given syringe 10 a distance of 10 cm is equated to a dose of 5 ml of medication for reception within the barrel 20.

Optionally, the software of the controller can be configured so as to permit variable overfill of medication within the syringe 10 based on customer preference. In other words, a given customer may wish for the medication to be slightly overfilled for each unit dose that is injected into the syringe 10. For example, for an application where 10 ml is to be delivered to the syringe 10, the controller will consult the calibration table to determine that the plunger needs to be extended 3 cm for a 10 ml dose and moreover, because the customer code that is preferably entered into the controller indicates that special customer instructions have been supplied by the customer, the controller determines that this customer has instructed that each dose be overfilled by 0.2 ml and this requires that the plunger 50 be extended 3.02 cm. The customer can enter the amount of overfill for each dose volume or the customer can instruct that the syringe 10 be overfilled across the board regardless of the size of the dose. In other words, the customer can instruct that for each dose filling, the syringe 10 is overfilled by 0.2 ml of medication. This amount of overfill is then equated to a modified distance that the plunger 50 is extended.

After the syringe 10 has been prepared by removing the tip cap 40 and extending the plunger 50 a prescribed distance, the syringe 10 is then delivered to a fluid transfer station where a fluid transfer device 900 prepares and delivers the desired amount of medication.

Figure 11:
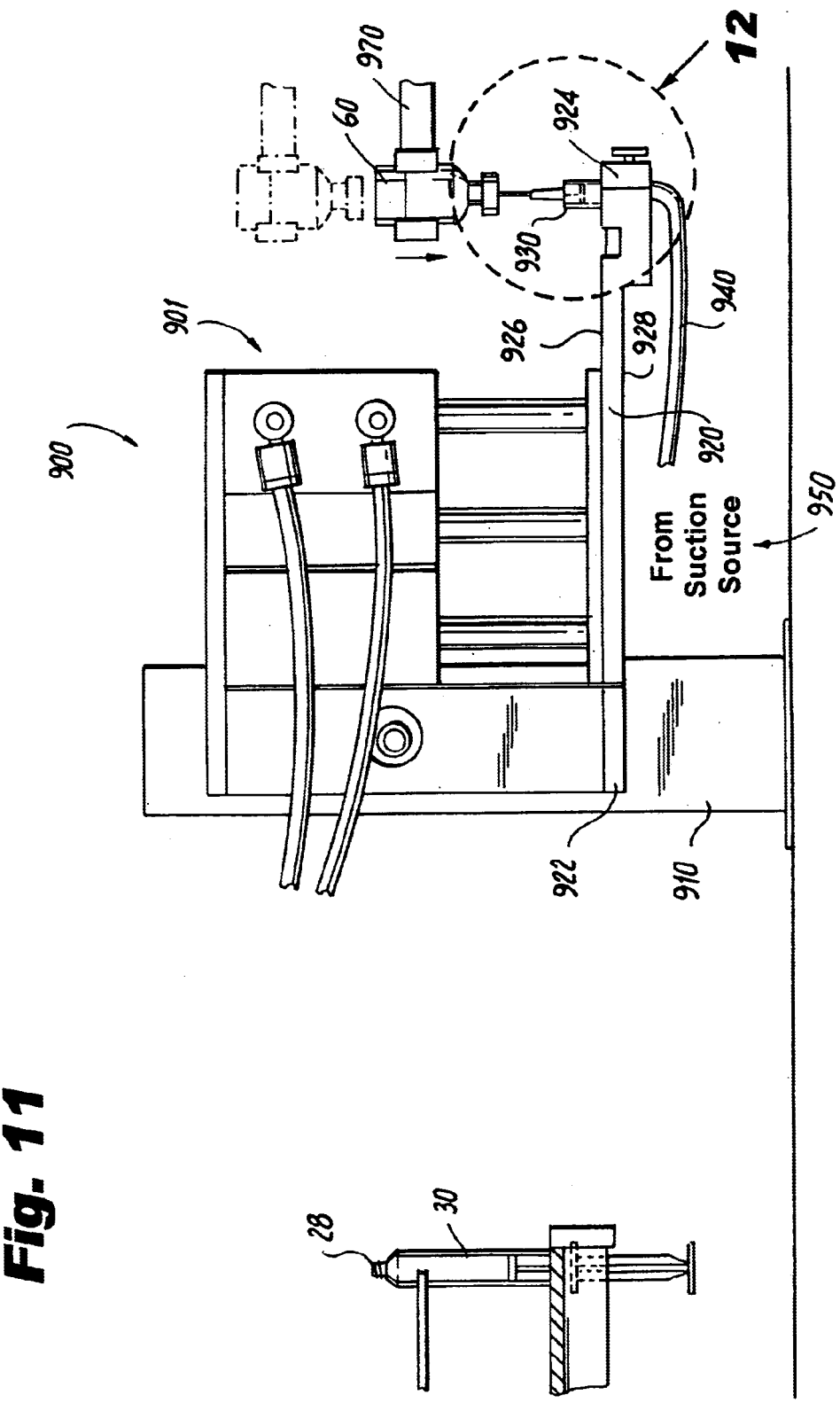
FIG. 11 is a side elevation view of an automated fluid transfer device for preparing and delivering medication from the vial of FIG. 2 to the open syringe.

FIG. 11 is a side elevation view of the automated fluid transfer device 900 for preparing and delivering the medication to the barrel chamber 30 for storage therein. The device 900 is part of the previously mentioned fluid transfer station. The device 900 is a controllable device that is operatively connected to a control unit, such as a computer, which drives the device 900 to specific locations at selected times. The control unit can be a personal computer that runs one or more programs to ensure the coordinated operation of all of the components of the system 100.

Figure 13:
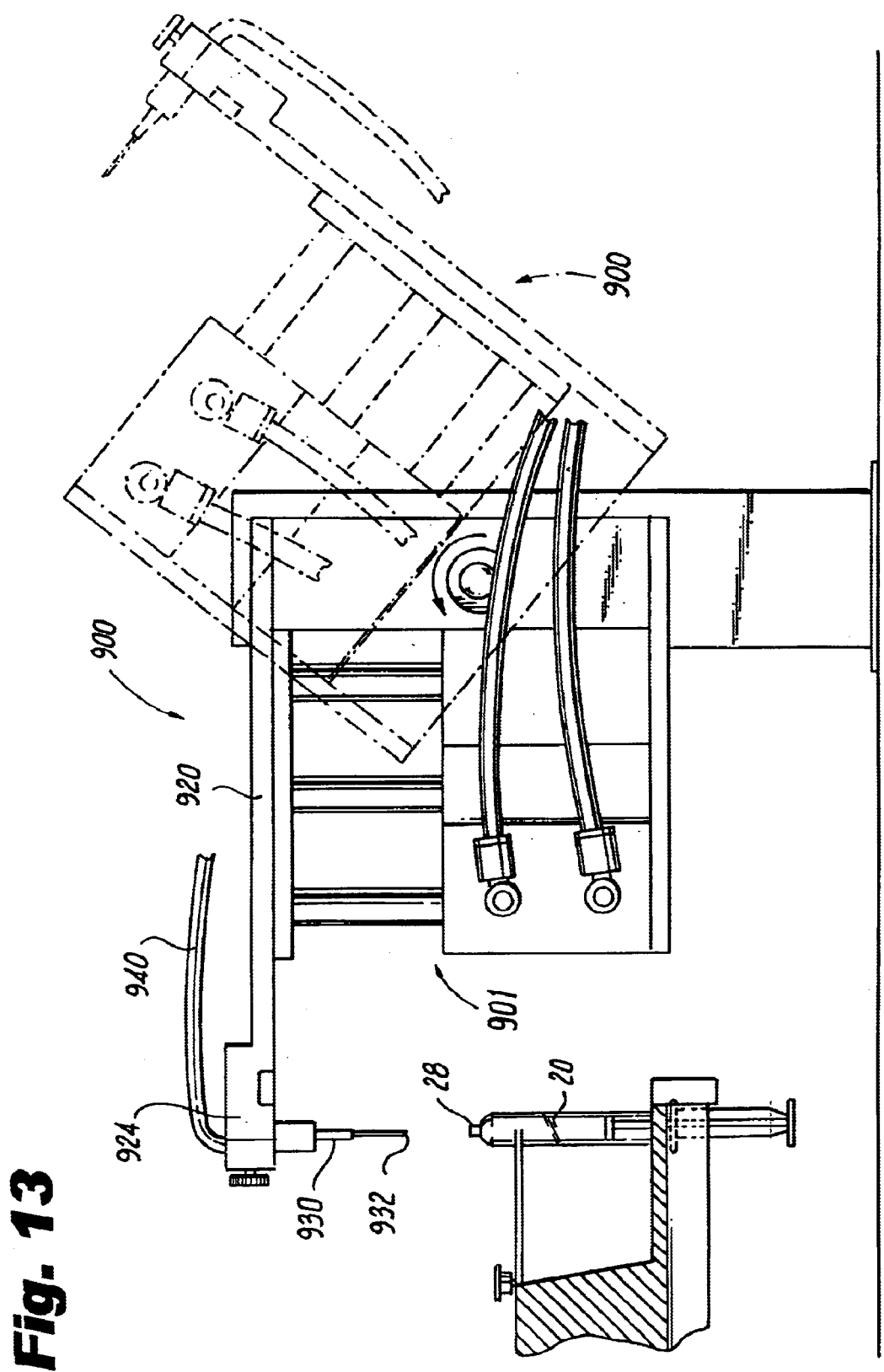
FIG. 13 is a side elevation view of the device of FIG. 11 in a rotated position with the cannula being in a position for delivery of the medication to the syringe.
Figure 14:
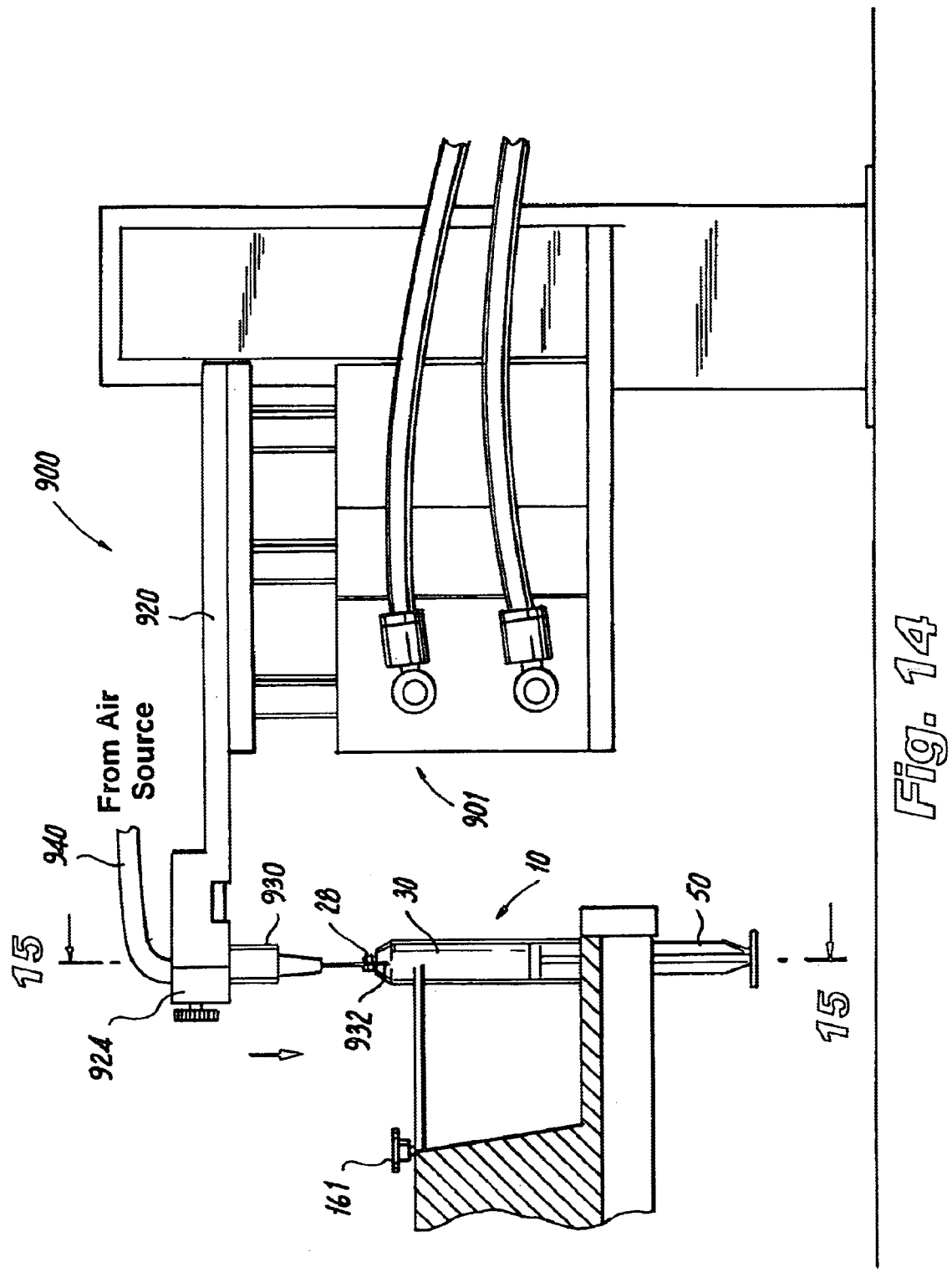
FIG. 14 is a side elevation view of the device of FIG. 13 being lowered so that the cannula is inserted into the syringe.

In one exemplary embodiment, the automated device 900 is a robotic device and includes an actuator for manipulating the moving components thereof. The device 900 includes a support post 910 that has a first end and an opposing second end. A pivotable arm 920 is pivotally mounted to the support post 910 so that the arm 920 has a degree of rotational freedom about the support post 910. The arm 920 includes a first section 922 that is pivotally mounted at its one end to the support post 910 and at its other end, the first section 922 is connected to an elongated platform. The arm 920 and the elongated platform 924 thereof have a first face 926 and an opposing second face 928. The arm 920 generally pivots between a first position where the first face 926 faces in an upward direction, as shown in FIG. 11, and a second position in which the first face 926 faces in a downward direction, as shown in FIG. 13. In other words, the platform 924 is turned upside down as the arm 920 pivots between the first and second positions: The device 900 can be driven by any number of automated drive systems, including the use of an electric motor, hydraulic means, pneumatic means, etc., and in one exemplary embodiment, the device is driven between the first and second positions using a number of different components that permit different movements. For example, one drive mechanism can pivot the entire device 900 so that the arm 920 pivots between the first and second positions and another mechanism, such as a hydraulic or pneumatic system 901, can be used to ensure that the arm 920 is properly lowered into the desired position relative to the syringe 10. For example, the system 901 is responsible for the up and down motion of the arm 920 and it also serves as a guide mechanism since the system 901 causes the arm 920 to be lowered into the correct position relative to the syringe 10.

The support post 910 is preferably stationary as the first section 922 pivots thereabout; however, in an alternative embodiment, the support post 910 can be permitted a degree of movement by incorporating the support post 910 into the robotic system such that the first end of the support post 910 is connected to a base that can travel within one or more guide members to permit the entire device 900 to move in at least one and preferably several directions.

The platform 924 has an opening formed therein and a cannula or similar type instrument 930 is disposed therein. The cannula 930 has an open tip 932 and when it is disposed and secured within the opening of the platform 924, the cannula 930 is generally perpendicular to the platform 924. The cannula 930 is operatively connected to a hose 940 that is attached to an aspirating device, indicated generally at 950 (these components form a cannula set). The aspirating device 950 is designed to apply negative pressure within the hose 940 and also within the passageway of the cannula 930. By applying negative pressure (suction) within the hose 940, fluid can be drawn into the passageway of the cannula 930 as well as into the hose 940.

The aspirating device 950 is constructed to aspirate a prescribed amount of medication from the vial 60. The vial 60 holds the medication after it has been prepared at one of the other stations of the system 100. More specifically, the medication can be prepared by first taking a predetermined amount of solid medication and then dissolving and diluting it with a diluent to form medication in the liquid state. Prepared medication is typically stored in the vial 60 or the like and therefore, in one exemplary embodiment, the vial 60 is a glass vial having a pierceable septum or membrane 64 that extends across the open end of the vial 60. As part of the medication preparation process, the medication is reconstituted by mixing the contents of the vial 60 using conventional techniques. For purpose of illustration only, the vial 60 holding the reconstituted medication is held by a robotic gripper 970 or the like which can pivot and otherwise deliver the vial 60 to a predetermined location. Means 971 (FIG. 12) for releasably locking the cannula 930 in place is provided. For example, the means 971 can be a rotatable fastener (e.g., screw) that securely holds the cannula 930 in place in the opening in the platform 924 when it the fastener 971 engages a side wall of the cannula 930.

Figure 12:
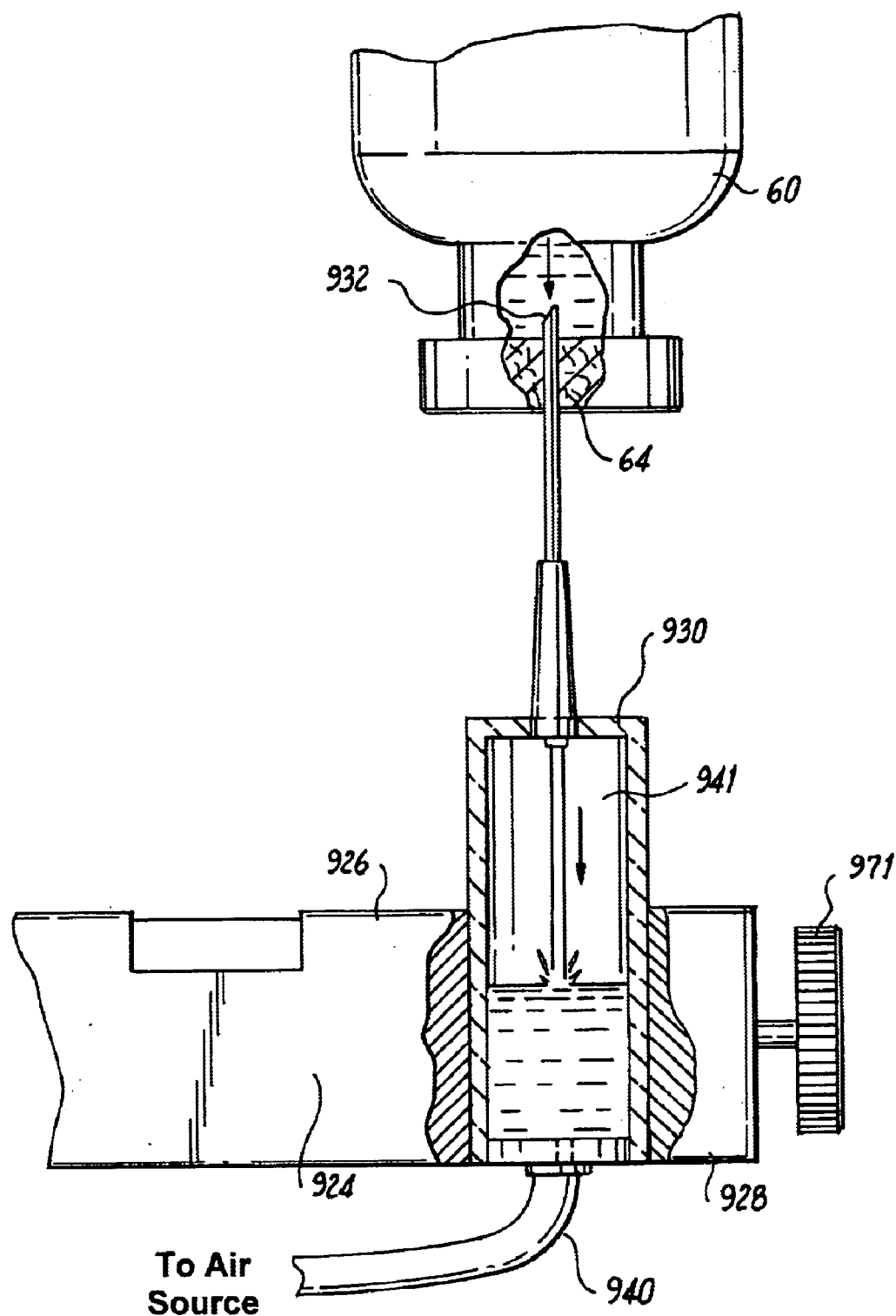
FIG. 12 is a close up view of the device of FIG. 11 showing aspiration of medication from the vial to the syringe.

For example, the vial 60 is preferably held upside down by the gripper 970 (with the medication contents being contained within the vial 60 by the septum/membrane) and the gripper 970 is lowered down by a control unit until the cannula 930 pierces the septum/membrane of the vial 60. FIG. 12 is a close up view of the aspiration process. As soon as the cannula 930 pierces the septum/membrane, the fluid medication is free to flow into the cannula 930 from the interior of the vial 60. At the same time that the vial 60 is brought into contact with the cannula 930 to cause piercing of the septum/membrane, the aspirating device 950 is turned on and negative pressure exists within the hose 940. The presence of negative pressure within the hose 940 causes aspiration of the medication through the cannula 930 and into a storage means 941. For example, the storage means 941 can be in the form of a compartment or the like where the aspirated medication is stored as shown in the Figures. A predetermined amount of the medication is aspirated from the vial 60 and the amount aspirated depends upon the size of the unit dose of the medication that is needed to be delivered to the patient. In any event, the volume of medication aspirated is preferably greater than the volume of medication that is needed for the unit dose since some of the medication may be left behind on the surfaces of the equipment, etc.

After the medication has been aspirated into the cannula 930, the arm 920 is pivoted from the first position shown in FIG. 11 to the second position shown in FIG. 13 while the aspirating device goes to pressure neutral until it is ready to dispense the dose. FIG. 13 shows this pivoting action in detail. As previously mentioned, in one exemplary embodiment, the arm 920 pivots so that the elongated platform 924 is turned upside down and as a result, in the second position, the cannula 930 faces downward and the hose 940 faces upward.

The device 900 is then moved to a dispensing location as by moving the support post 910 or base attached thereto within a guide member so that the cannula 930 is brought towards the dial 130 and more specifically, the cannula 930 is brought into alignment with the uncapped, open tip section 28 of the syringe barrel 20. Preferably, one or more sensors are used to detect and signal when the cannula 930 is properly aligned with the tip section 28. For example, one sensor can detect when the cannula 930 lies within a certain plane that aligns with the open tip 28 and the sensor will then signal the controller 970 of such alignment. After receiving the signal, the controller instructs the device 900 to lower the cannula 930 into the syringe barrel 20.

Figure 15:
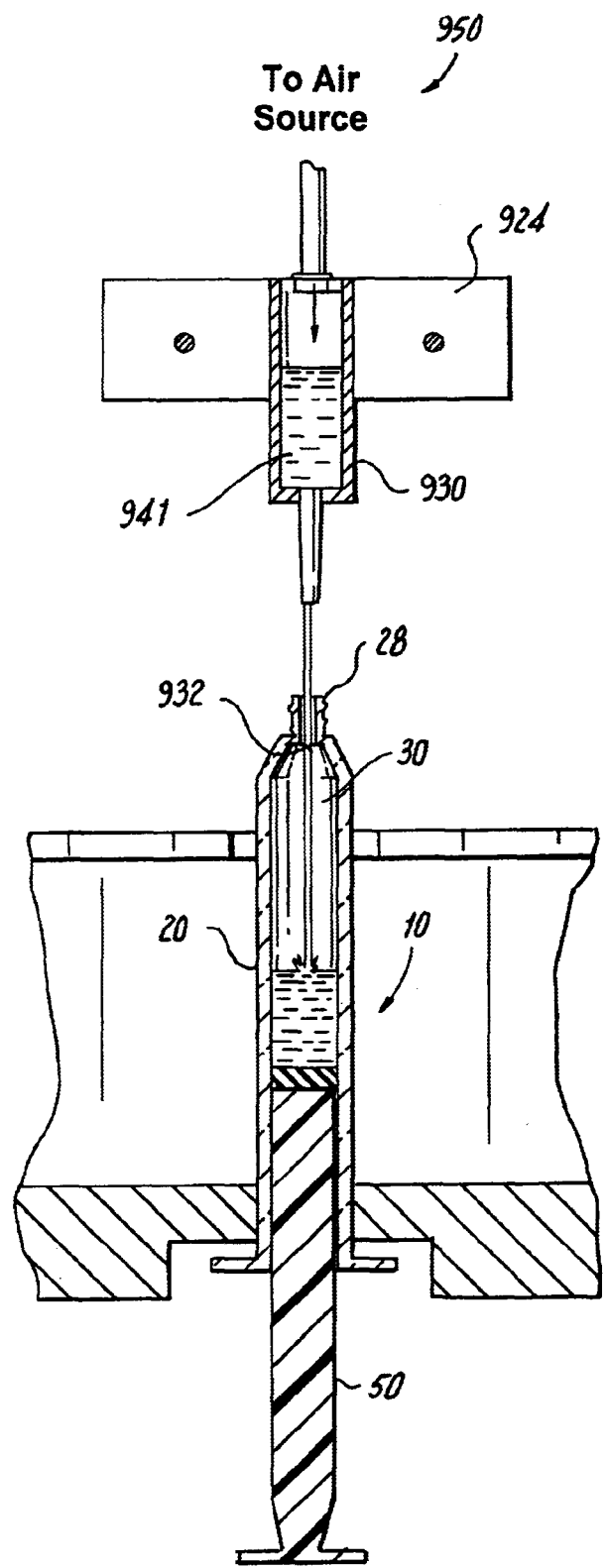
FIG. 15 is a cross-sectional view taken along the line 15—15 of FIG. 14.

Once the cannula 930 is axially aligned with the opening/passageway formed in the barrel tip 28, the cannula 930 is lowered so that at least the tip 932 thereof is disposed within the barrel chamber 30 as shown in FIGS. 15 and 16. The aspirated medication that is being held by the device 900 is then discharged through the cannula 930 and into the barrel chamber 30. By removing the negative pressure condition from within the hose 940 and the needle 930, the medication is permitted to flow out of the cannula 930 and into the barrel chamber 30. Preferably, the aspirating device 950 is also capable of applying a positive pressure within the hose 940 to assist the medication in being discharged from the cannula 930 into the barrel chamber 30. The aspirated medication is thus injected into the barrel 20 of the syringe 10 as shown in FIG. 15. It will also be appreciated that a dilution step could be implemented where the medication is diluted as it is dispensed into the barrel 20. For example, a concentrated form of the medication can be injected first into the barrel 20 through a first cannula 930 and then a diluent can be dispensed through a second needle (not shown) that forms a part of the same robotic device 900 or another robotic device 900. Precise quantities of both concentrated medication and diluent are injected into the barrel 20 so that the resulting medication has the desired concentration and volume. Alternatively, the medication can be diluted by supplying another vial 60 that contains the diluent to the cannula 930. More specifically, the cannula 930 contains the aspirated, concentrated form of the reconstituted drug and then another vial 60 containing diluent is brought into position relative to the cannula 930 such that the tip 932 pierces this diluent vial 60 and then a prescribed amount of diluent is aspirated into the cannula 930, thereby diluting the concentrated reconstituted drug.

The aspirating device 950 can be configured so that it discharges a precise quantity of the medication. The aspirating device 950 thus can have a flow meter or other type of measuring device or equipment that permits the volume of discharged medication to be determined. Because the aspirating device 950 is part of an overall programmable robotic system, the user inputs the precise quantity of medication that is needed and the aspirating device 950 only dispenses this quantity through the cannula 930 and into the barrel chamber 30.

After the aspirated medication is injected into the barrel chamber 30, the arm 920 is moved upward so that the cannula 930 is retracted from the barrel 20. Once the cannula 930 clears the syringe 10, the robotic arm 920 can pivot back to the first position where the cannula 930 faces upward. Once again, one or more sensors can be used to detect that the cannula 930 has cleared the syringe 10.

Prior to its next use, the cannula 930 is cleaned using conventional techniques. One exemplary method of cleaning the cannula 930 is described in commonly owned pending U.S. patent application Ser. No. 09/999,188, filed Nov. 30, 2001, which is hereby incorporated by reference in its entirety.

As previously mentioned, the seventh station 180 also includes a device 300 for replacing the tip cap 40 on the syringe 10 after the syringe 10 is filled with the medication, etc. at the above described earlier station, e.g., third station 150. The device 300 that is used at the third station 150 for removing and parking the tip cap 40 from the syringe 10 prior to the syringe being filled is generally the same type of device as the device 300 that is used at seventh station 180 for retrieving the tip cap 40 from the pin 161 and then replacing it on the syringe 10. The steps of operation are slightly different at the seventh station 180 since the tip cap 40 is initially retained on the pin 161 and not the syringe 10 at this station.

In the starting position at the seventh station 180, the second pneumatic control device 600 is activated while the first pneumatic control device 441 and the third pneumatic control device 630 are both deactivated (valves are closed) so that the vertical base 410 is in the raised position as well as being in the in position. Thus, the gripper arms 440 are generally above the pin 161 since the vertical base 410 is in the in position. The first pneumatic control 441 is preferably in the closed position so that the gripper arms 440 are closed with respect to one another. The first pneumatic control 441 is activated and the third pneumatic control device 630 is then activated so that the gripper arms 400 open and the vertical base 410 goes from the raised position to the lowered position. In the lowered position, the gripper arms 440 surround the tip cap 40 that is resting on the pin 161. Next, the first pneumatic control 441 is deactivated resulting in the gripper arms 440 closing and securely capturing and retaining the tip cap 40. In other words, the tip cap 40 nests within the gripper arms 440 and is ready to be removed and lifted from the pin 161. At this point in time, the sensor device 483 is preferably used to determine whether the tip cap 40 is present between the gripper arms 440. If the tip cap 40 is present and is captured between the gripper arms 440, then the light beam of the sensor 483 is broken and a signal is delivered to the controller 470. The controller 470 will then instruct the gripper unit 400 to continue the tip cap replacement operation. If the sensor device 483 does not detect that the tip cap 40 is present between the gripper arms 440, the gripper arms 440 can be instructed to attempt the grasping process again or the controller 470 can be instructed to restart the entire operation by returning the vertical base 410 to the starting position and then the dial 130 is advanced and then process is started over again to attempt to grasp and capture the tip cap 40 from the pin 161 so that it can be replaced onto a filled syringe 10.

To lift the tip cap 40 from the pin 161, the third pneumatic control device 630 is deactivated resulting in the vertical base 410 moving from the lowered position to the raised position. As the vertical base 410 is raised, the tip cap 40 is removed and lifted from the pin 161 since the tip cap 40 is securely held by the gripper arms 440. The vertical base 410 is moved to the raised position and then the second pneumatic control device 600 is activated causing the vertical base 410 to move from the in position to the out position. Thus, the vertical base 410 and the gripper arms 440 thereof are moved away from the dial 130 and the gripper arms 440 are moved from a position where they are disposed over the pin 161 to a position where they are disposed over the uncapped syringe 10. The uncapped syringe 10 has been previously filled with medication and therefore is ready to be capped.

To cap the syringe 10, the third pneumatic control device 630 is activated to cause the vertical base 410 to move from the raised position to the lowered position. When the vertical base 410 moves to the lowered position, the tip cap 40 is press fitted onto the barrel tip 28 of the uncapped syringe 10; however, the tip cap 40 is still securely held between the gripper arms 440. The first pneumatic control 441 is then activated to cause the gripper arms 440 to move from the closed position to the open position. When the gripper arms 440 open, the tip cap 40 is free from the gripper unit 400 and remains fixedly attached to the barrel tip 28 of the syringe 10. The vertical base 410 is then moved to the raised position by deactivating the third pneumatic control device 630 so that the gripper arms 440 are removed from the syringe 10 and are delivered to a position where the gripper arms 440 are disposed above and spaced from the barrel tip 28 of the syringe 10. To start the replacing operation again, the vertical base 410 is returned to the starting position by deactivating the second pneumatic control device 600 to cause the gripper arms 440 to move to the in position so that they are disposed above the dial 130 and more specifically, above the path that the pin 161 follows as the dial 130 advances. The dial 130 is then advanced until a new tip cap 40 is disposed underneath the gripper arms 440 and then the process is started over.

The capped syringe 10 can then be transferred to other stations, such as a station where the syringe in bandolier form is cut into individual syringes 10 that are labeled for particular patients. The syringes 10 can then be unloaded from the dial 130 by a suitable mechanical device. The syringe 10 is then further processed as for example by being delivered to a storage receptacle where it is stored or by being delivered to a transporting device for delivery to the patient.

Thus, the above described system is one which is fully automated and includes a number of different stations where different operations are performed at each station. This greatly improves the efficiency of the system and reduces human error, while still offering the range of options that are desirable in such operations.

It will be appreciated by persons skilled in the art that the present invention is not limited to the embodiments described thus far with reference to the accompanying drawings; rather the present invention is limited only by the following claims.

What is claimed is:

1. An automated device for extending a plunger of a syringe a defined distance within a syringe barrel based upon inputted syringe information, the device comprising:

a housing;

an adjustable plunger extension mechanism that includes a movable component that intimately engages the plunger so that movement of the component is translated into extension of the plunger, the component including a controllable drive that moves the component the defined distance;

a controller that receives the inputted syringe information and calculates the defined distance that the plunger is moved based on the inputted syringe information and instructs the controllable drive to move the plunger the defined distance; and a sensor device for monitoring a length of travel of the movable component, the sensor device being independent and stationary relative to the movable component.

2. The automated device of claim 1, wherein the sensor device signals the controller when the component reaches one end of its permitted path of travel, the controller in communication with the controllable drive to instruct the drive to cease moving the component in a specific direction when the component reaches one end of its permitted path of travel.

3. The automated device of claim 1, wherein the adjustable plunger extension mechanism includes a support frame, a carrier that moves linearly therealong and includes a pair of arms that engage the plunger.

4. The automated device of claim 1, wherein the controllable drive comprises a servo motor and a screw drive mechanism that is operatively coupled to the carrier so that actuation of the servo motor is translated into movement of a drive spindle of the screw drive mechanism which in turn causes movement of the component.

5. The automated device of claim 4, wherein the servo motor rotates in a first direction and in a second opposite direction such that rotation in the first direction causes the component to move linearly in a first direction and rotation in the second direction causes the component to move linearly in a second direction.

6. The automated device of claim 1, wherein the controllable drive comprises a servo motor whose actuation causes the servo motor to go through a predetermined number of steps.

7. The automated device of claim 6, wherein the controller is operatively connected to the servo motor and sends a control signal to the servo motor to instruct the servo motor to go through a predetermined number of steps, wherein there is a correlation between the number of steps and the defined distance that the component is driven which in turn represents the defined distance that the plunger is extended creating a volume within the syringe to accept a prescribed volume of medication.

8. The automated device of claim 7, wherein the inputted syringe information includes a syringe type, a barrel diameter, and a desired dose volume of medication to be filled into the syringe, wherein the controller calculates the defined distance that the plunger needs to be extended based upon the inputted syringe information and then calculates the number of steps that the servo motor is driven through in order to extend the plunger the defined distance.

9. The automated device of claim 1, wherein the component includes first and second verticals walls that are connected at end thereof, the vertical walls being parallel to one another and spaced apart from one another, wherein other ends of the vertical walls include features for intimately engaging the plunger to cause the extension thereof when the component is moved linearly.

10. The automated device of claim 9, wherein the features comprise a pair of flange members disposed at the other ends of the vertical walls, each flange member extending beyond the vertical wall and into a space between the two parallel vertical walls so as to overhang the vertical wall, wherein a diameter of the plunger is less than a distance between the two spaced vertical walls but greater than a distance between the flange members so that the flange members grip and engage a lip of the plunger and cause the extension of the plunger.

11. The automated device of claim 10, wherein the component travels from a starting position in which the component is in a raised position and a lowered position where the component has traveled away from the raised position, the plunger being received within the space between the vertical walls in the starting position with the lip of the plunger being proximate to or seated against the flange members and wherein movement of the component from the starting position to the lowered position extends the plunger the desired defined distance prior to the syringe being removed from the automated device.

12. An automated device for extending a plunger of a syringe a defined distance within a syringe barrel based upon inputted syringe information, the device comprising:
   a housing;
   an adjustable plunger extension mechanism that includes a movable component that intimately engages the plunger so that movement of the component is translated into extension of the plunger, the component including a controllable drive that moves the component the defined distance;
   a controller that receives the inputted syringe information and calculates the defined distance that the plunger is moved based on the inputted syringe information and instructs the controllable drive to move the plunger the defined distance; and
   a sensor device that signals the controller when the component reaches one end of its permitted path of travel, the controller in communication with the controllable drive to instruct the drive to cease moving the component in a specific direction when the component reaches one end of its permitted path of travel, wherein the sensor device includes a first sensor fixed at a first location at one end of the permitted length of travel for the component and a second sensor fixed to a second location at the other end of the permitted length of travel, the sensors being constructed so that they detect the presence of the movable component.

13. The automated device of claim 12, wherein each of the first and second sensors comprises a U-shaped bracket sensor that emits a beam across two arms thereof with a section of the movable component being received between the two arms so as to impinge the beam and trigger the sensor device to send a control signal to a controller that is operatively coupled to the controllable drive.

14. The automated device of claim 13, wherein the section of the movable component that is received between the two arms is a flag that is coupled to the component and extends outwardly therefrom.

15. The automated device of claim 13, wherein the first and second sensors are linearly aligned and spaced apart from one another, the first sensor representing an upper limit of the path of travel of the component, the second sensor representing a lower limit of the path of travel of the component.

16. An automated device for extending a plunger of a syringe a defined distance within a syringe barrel, the device comprising:
   a housing;
   an adjustable plunger extension mechanism that includes a movable component that intimately engages the plunger so that movement of the component is translated into extension of the plunger; and
   an input for inputting syringe specific information that is used in part to calculate the defined distance the plunger is extended; and
   a controller that receives the inputted syringe information and calculates the defined distance that the plunger is moved based on the inputted syringe information and determines drive parameters that are delivered to a drive that is operatively connected to the movable component to cause the plunger to be moved the defined distance, wherein the inputted syringe information includes a variable fluid volume overfill value that factors into the calculation of the defined distance.

17. The automated device of claim 16, wherein the drive comprises a servo motor and one of the drive parameters is a number of steps through which the servo motor is to be driven to cause the plunger to be extended the defined distance, wherein there is a correlation between the number of steps through which the drive is driven and the distance that the plunger is extended.

18. The automated device of claim 16, wherein the controller calculates the defined distance based in part upon a volume of the prescribed dose and a diameter of the syringe barrel so that the plunger is extended sufficiently to form a space that has a volume that at least equals the volume of the prescribed dose of medication.

19. An automated device for extending a plunger of a syringe a defined distance within a syringe barrel, the device comprising:
   a housing;
   an adjustable plunger extension mechanism that includes a movable component that intimately engages the plunger so that movement of the component is translated into extension of the plunger; and
   an input for inputting syringe specific information that is used in part to calculate the defined distance the plunger is extended; and a controller that receives the inputted syringe information and calculates the defined distance that the plunger is moved based on the inputted syringe information and determines drive parameters that are delivered to a drive that is operatively connected to the movable component to cause the plunger to be moved the defined distance, wherein the inputted syringe information includes an overdraw value that is added to an inputted dose volume to form a total fluid volume that is used as a basis for calculating the defined distance.

20. The automated device of claim 19, wherein the overdraw value comprises a volume of an air gap to be added to the syringe barrel to assist in filling of the syringe barrel.

* * * * *